(12) United States Patent
Lavik et al.

(10) Patent No.: US 12,171,885 B2
(45) Date of Patent: Dec. 24, 2024

(54) HEMOSTATIC NANOCAPSULES FOR STOPPING BLEEDING, VISUALIZING INJURY, AND DELIVERING DRUGS

(71) Applicant: UNIVERSITY OF MARYLAND, BALTIMORE COUNTY, Baltimore, MD (US)

(72) Inventors: Erin Lavik, Ellicott City, MD (US); Nuzhat Maisha, Halethorpe, MD (US)

(73) Assignee: UNIVERSITY OF MARYLAND, BALTIMORE COUNTY, Baltimore, MD (US)

( * ) Notice: Subject to any disclaimer, the term of this patent is extended or adjusted under 35 U.S.C. 154(b) by 18 days.

(21) Appl. No.: 17/812,746

(22) Filed: Jul. 15, 2022

(65) Prior Publication Data
US 2023/0018837 A1 Jan. 19, 2023

Related U.S. Application Data

(60) Provisional application No. 63/222,044, filed on Jul. 15, 2021.

(51) Int. Cl.
*A61K 9/51* (2006.01)
*A61K 9/19* (2006.01)

(52) U.S. Cl.
CPC .............. *A61K 9/5146* (2013.01); *A61K 9/19* (2013.01)

(58) Field of Classification Search
CPC ................................ A61K 9/5146; A61K 9/19
See application file for complete search history.

(56) References Cited

U.S. PATENT DOCUMENTS

2013/0196071 A1* 8/2013 Yang ........................ C09D 7/70
427/386

FOREIGN PATENT DOCUMENTS

| CN | 106701058 A | * | 5/2017 | |
|---|---|---|---|---|
| EP | 3539564 A1 | * | 9/2019 | ......... A61K 39/0008 |
| WO | WO-2009105231 A1 | * | 8/2009 | ............. A61K 38/17 |

OTHER PUBLICATIONS

Machine Translation of CN106701058A (Year: 2017).*
Lashof-Sullivan et al.; Hemostatic Nanoparticles Improve Survival Following Blunt Trauma Even after 1 Week Incubation at 50° C.; ACS BiomaterSci Eng. Mar. 14, 2016; 2(3): 385-392. doi:10.1021/acsbiomaterials.5b00493. (Year: 2016).*
Sirsi et al.; State-of-the-art materials for ultrasound-triggered drug delivery; Advanced Drug Delivery Reviews 72 (2014) 3-14. (Year: 2014).*
Batyrbekov et al; Segmented Polyurethane/Collagen Blends for Biomedical Application; Mater. Res. Soc. Symp. Proc. vol. 897E © 2006 Materials Research Society. (Year: 2006).*
Povey; Ultrasound particle sizing: A review; Particuology 11 (2013) 135-147. (Year: 2013).*
Abdel-Rahman et al., Sonochemical synthesis, DNA binding, antimicrobial evaluation and in vitro anticancer activity of three new nano-sized Cu(II), Co(II) and Ni(II) chelates based on tri-dentate NOO imine ligands as precursors for metal oxides. J Photochem Photobiol B. Sep. 2016;162:298-308.
Benjamini, E., Immunology: a short course. vol. 77. Cannot Locate.
Bernacca et al., In vitro blood compatibility of surface-modified polyurethanes. Biomaterials. Jul. 1998;19(13):1151-65.
Bertram et al., Intravenous hemostat: nanotechnology to halt bleeding. Sci Transl Med. Dec. 16, 2009;1(11):11ra22. 17 pages.
Boffito et al., Hybrid Injectable Sol-Gel Systems Based on Thermo-Sensitive Polyurethane Hydrogels Carrying pH-Sensitive Mesoporous Silica Nanoparticles for the Controlled and Triggered Release of Therapeutic Agents. Front Bioeng Biotechnol. May 19, 2020;8:384. 24 pages.
Cardenas et al., Mechanisms of trauma-induced coagulopathy. Curr Opin Hematol. Sep. 2014;21(5):404-9.
Chanan-Khan et al., Complement activation following first exposure to pegylated liposomal doxorubicin (Doxil): possible role in hypersensitivity reactions. Ann Oncol. Sep. 2003;14(9):1430-7.
Cherng et al., Polyurethane-based drug delivery systems. Int J Pharm. Jun. 25, 2013;450(1-2):145-62.
Cloonan. Treating traumatic bleeding in a combat setting. Mil Med. Dec. 2004;169(12 Suppl):8-10.
Cullion et al., Ultrasound-triggered liposomes for on-demand local anesthesia. Ther Deliv. Jan. 2018;9(1):5-8.
Ember et al., The human complement system in health and disease. Marcel Dekker 1998, pp. 241-284.
Fearon et al., Activation of the alternative complement pathway due to resistance of zymosan-bound amplification convertase to endogenous regulatory mechanisms. Proc Natl Acad Sci U S A. Apr. 1977;74(4):1683-7.
Fernandez-Moure et al., The Chemistry of Lyophilized Blood Products. Bioconjug Chem. Jul. 18, 2018;29(7):2150-2160.
Gando et al., Disseminated intravascular coagulation. Nat Rev Dis Primers. Jun. 2, 2016;2:16037. 1-16.
Guo et al., The role of surfactant and costabilizer in controlling size of nanocapsules containing TEGDMA in miniemulsion. Journal of Wuhan University of Technology—Mater. Sci. Ed. 2009, 24 (6), 1004-1006.

(Continued)

*Primary Examiner* — Robert A Wax
*Assistant Examiner* — John W Lippert, III
(74) *Attorney, Agent, or Firm* — Casimir Jones, SC; Tristan A. Fuierer

(57) ABSTRACT

One of the significant challenges to translation of intravenously administered nanomaterials has been complement-mediated infusion reactions which can be lethal. Slow infusions can reduce infusion reactions, but slow infusions are not always possible in applications like controlling bleeding following trauma. Nanocapsules based on polyurethane are introduced as candidates that do not substantially activate complement protein C5a and the PEGylation and functionalization of the nanocapsules with the GRGDS peptide to create a new class of hemostatic nanomaterials is disclosed. Advantageously, the nanocapsules substantially avoid complement-mediated infusion reactions, promote faster clotting than controls, maintain maximum clot firmness, and do not activate pro-inflammatory cytokines.

16 Claims, 11 Drawing Sheets

(56) References Cited

OTHER PUBLICATIONS

Hamad et al., Complement activation by PEGylated single-walled carbon nanotubes is independent of C1q and alternative pathway turnover. Mol Immunol. Aug. 2008;45(14):3797-803.
Hamad et al., Distinct polymer architecture mediates switching of complement activation pathways at the nanosphere-serum interface: implications for stealth nanoparticle engineering. ACS Nano. Nov. 23, 2010;4(11):6629-38.
Hubbard et al., Hemostatic nanoparticles increase survival, mitigate neuropathology and alleviate anxiety in a rodent blast trauma model. Sci Rep. Jul. 13, 2018;8(1):10622.
Hubbard et al., Steroid-Loaded Hemostatic Nanoparticles Combat Lung Injury after Blast Trauma. ACS Macro Lett. Apr. 21, 2015;4(4):387-391.
Innerhofer et al., Reversal of trauma-induced coagulopathy using first-line coagulation factor concentrates or fresh frozen plasma (RETIC): a single-centre, parallel-group, open-label, randomised trial. Lancet Haematol. Jun. 2017;4(6):e258-e271.
Jeremias Junior et al., Low-intensity pulsed ultrasound accelerates healing in rat calcaneus tendon injuries. J Orthop Sports Phys Ther. Jul. 2011;41(7):526-31.
Kamimura et al., Focused ultrasound neuromodulation of cortical and subcortical brain structures using 1.9 MHz. Med Phys. Oct. 2016;43(10):5730. 6 pages.
Kauvar et al., Impact of hemorrhage on trauma outcome: an overview of epidemiology, clinical presentations, and therapeutic considerations. J Trauma. Jun. 2006;60(6 Suppl):S3-11.
King et al., Changes in intracranial pressure, coagulation, and neurologic outcome after resuscitation from experimental traumatic brain injury with hetastarch. Surgery. Aug. 2004;136(2):355-63.
Kumar. Coagulopathy associated with traumatic brain injury. Curr Neurol Neurosci Rep. Nov. 2013;13(11):391.
Lashof-Sullivan et al., Hemostatic Nanoparticles Improve Survival Following Blunt Trauma Even after 1 Week Incubation at 50° C. ACS Biomater Sci Eng. Mar. 14, 2016;2(3):385-392.
Legon et a., Neuromodulation with single-element transcranial focused ultrasound in human thalamus. Hum Brain Mapp. May 2018;39(5):1995-2006.
Maisha et al., Development of a Sensitive Assay to Screen Nanoparticles in vitro for Complement Activation. ACS Biomater Sci Eng. Sep. 14, 2020;6(9):4903-4915.
Maisha et al., Getting to the Core of it all: Nanocapsules to mitigate infusion reactions can promote hemostasis and be a platform for intravenous therapies. Nano Lett. 2021, 21, 9069-9076.
Maisha et al., Getting to the Core of it all: Nanocapsules to mitigate infusion reactions can promote hemostasis and be a platform for intravenous therapies. Supplemental Material for Nano Lett. 2021, 21, 9069-9076. 11 pages.
Menikheim et al., On-Demand and Long-Term Drug Delivery from Degradable Nanocapsules. ACS Appl Bio Mater. Nov. 16, 2020;3(11):7369-7375.
Moghimi et al., Complement activation turnover on surfaces of nanoparticles. Nano Today. Aug. 2017;15:8-10.
Niu et al., Facile fabrication of polyurethane microcapsules carriers for tracing cellular internalization and intracellular pH-triggered drug release. Colloids Surf B Biointerfaces. May 1, 2017;153:160-167.
Okada et al., Revision of 'golden hour' for hemodynamically unstable trauma patients: an analysis of nationwide hospital-based registry in Japan. Trauma Surg Acute Care Open. Mar. 10, 2020;5(1):e000405. 5 pages.
Onwukwe et al., Engineering Intravenously Administered Nanoparticles to Reduce Infusion Reaction and Stop Bleeding in a Large Animal Model of Trauma. Bioconjug Chem. Jul. 18, 2018;29(7):2436-2447.
Ouyang et al., Synthesis and characterization of triethylene glycol dimethacrylate nanocapsules used in a self-healing bonding resin. J Dent. Dec. 2011;39(12):825-33.

Peng et al., The role of anaphylatoxins C3a and C5a in regulating innate and adaptive immune responses. Inflamm Allergy Drug Targets. Jul. 2009;8(3):236-46.
Pramanik et al., Mitochondria Targeting Non-Isocyanate-Based Polyurethane Nanocapsules for Enzyme-Triggered Drug Release. Bioconjug Chem. Nov. 21, 2018;29(11):3532-3543.
Ricklin et al., Complement in immune and inflammatory disorders: pathophysiological mechanisms. J Immunol. Apr. 15, 2013;190(8):3831-8.
Rocas et al., Improved pharmacokinetic profile of lipophilic anticancer drugs using αvβ3-targeted polyurethane-polyurea nanoparticles. Nanomedicine. Feb. 2018;14(2):257-267.
Ruhnke et al., MR-guided HIFU treatment of symptomatic uterine fibroids using novel feedback-regulated volumetric ablation: effectiveness and clinical practice. Rofo. Oct. 2013;185(10):983-91.
Ruiz et al., Understanding the Influence of a Bifunctional Polyethylene Glycol Derivative in Protein Corona Formation around Iron Oxide Nanoparticles. Materials (Basel). Jul. 10, 2019;12(14):2218.
Samuels et al., Severe traumatic brain injury is associated with a unique coagulopathy phenotype. J Trauma Acute Care Surg. Apr. 2019;86(4):686-693.
Sanchez Ramirez et al., Antibacterial properties of polypyrrole-treated fabrics by ultrasound deposition. Mater Sci Eng C Mater Biol Appl. Sep. 2019;102:164-170.
Shoffstall et al., Intravenous hemostatic nanoparticles increase survival following blunt trauma injury. Biomacromolecules. Nov. 12, 2012;13(11):3850-7.
Shoffstall et al., Tuning ligand density on intravenous hemostatic nanoparticles dramatically increases survival following blunt trauma. Biomacromolecules. Aug. 12, 2013;14(8):2790-7.
Sodipo et al., One minute synthesis of amino-silane functionalized superparamagnetic iron oxide nanoparticles by sonochemical method. Ultrason Sonochem. Jan. 2018;40(Pt A):837-840.
Stewart et al., Clinical outcomes of focused ultrasound surgery for the treatment of uterine fibroids. Fertil Steril. Jan. 2006;85(1):22-9.
Szebeni et al, A porcine model of complement-mediated infusion reactions to drug carrier nanosystems and other medicines. Adv Drug Deliv Rev. Dec. 2012;64(15):1706-16.
Szebeni et al., Prevention of infusion reactions to PEGylated liposomal doxorubicin via tachyphylaxis induction by placebo vesicles: a porcine model. J Control Release. Jun. 10, 2012;160(2):382-7.
Szebeni. Hemocompatibility testing for nanomedicines and biologicals: predictive assays for complement mediated infusion reactions. European Journal of Nanomedicine 2012, 4 (1), 33-53.
Vlaisavljevich et al., Effects of Droplet Composition on Nanodroplet-Mediated Histotripsy. Ultrasound Med Biol. Apr. 2016;42(4):931-46.
Vlaisavljevich et al., Effects of Ultrasound Frequency on Nanodroplet-Mediated Histotripsy. Ultrasound Med Biol. Aug. 2015;41(8):2135-47.
Vlaisavljevich et al., Image-guided non-invasive ultrasound liver ablation using histotripsy: feasibility study in an in vivo porcine model. Ultrasound Med Biol. Aug. 2013;39(8):1398-409.
Wang et al., Activation of Human Complement System by Dextran-Coated Iron Oxide Nanoparticles Is Not Affected by Dextran/Fe Ratio, Hydroxyl Modifications, and Crosslinking. Front Immunol. Oct. 10, 2016;7:418.
Wibroe et al., Bypassing adverse injection reactions to nanoparticles through shape modification and attachment to erythrocytes. Nat Nanotechnol. Jul. 2017;12(6):589-594.
Xiang et al., Inhibition of Inflammation-Associated Thrombosis with ROS-Responsive Heparin-DOCA/PVAX Nanoparticles. Macromol Biosci. Aug. 2019;19(8):e1900112. 1-9.
Xu et al., Acoustic disruption of tumor endothelium and on-demand drug delivery for cancer chemotherapy. Nanotechnology. Apr. 12, 2019;30(15):154001. 18 pages.
Yang et al., Sonochemical assisted synthesis of dual functional BSA nanoparticle for the removal of excessive bilirubin and strong anti-tumor effects. Mater Sci Eng C Mater Biol Appl. Jul. 2019;100:688-696.

(56) References Cited

OTHER PUBLICATIONS

Yeung et al., Pulsed ultrasound treatment accelerates the repair of Achilles tendon rupture in rats. J Orthop Res. Feb. 2006;24(2):193-201.

Zhou et al., The degradation and biocompatibility of pH-sensitive biodegradable polyurethanes for intracellular multifunctional antitumor drug delivery. Biomaterials. Mar. 2012;33(9):2734-45.

* cited by examiner

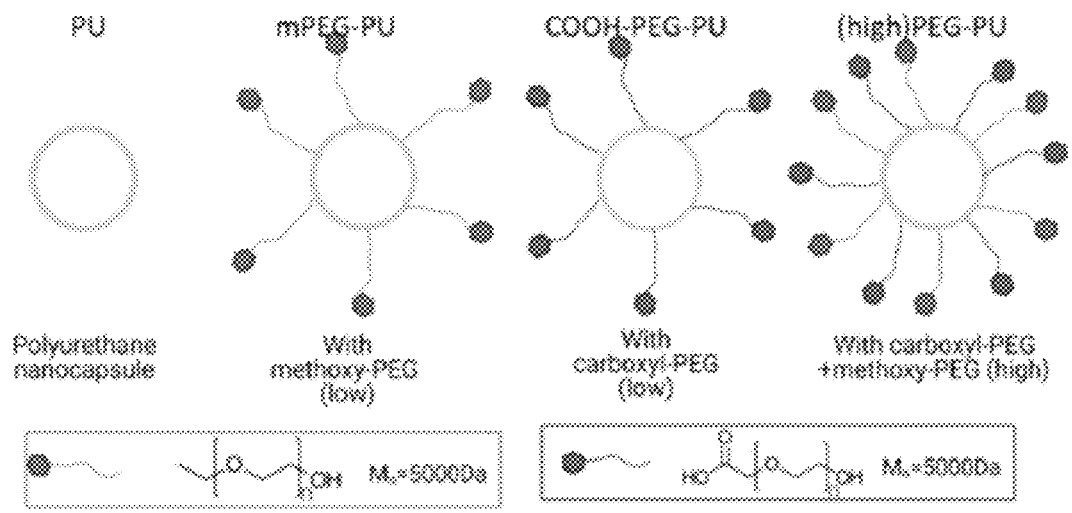
FIGURE 2A
| | PU | mPEG-PU | COOH-PEG-PU | (high)PEG-PU |
|---|---|---|---|---|
| Size (nm) | 254.4±65 | 186.5±5.5 | 263±34.5 | 252.6±66.8 |
| Zeta-Potential (mV) | -47±3.3 | -38.5±1.1 | -27.5±1.2 | -38.7±1.9 |
| Moles PEG/ Moles IPDI | | 1mole PEG/419 moles of IPDI | 1mole PEG/512 moles of IPDI | 1mole PEG/149 moles of IPDI |
FIGURE 2B
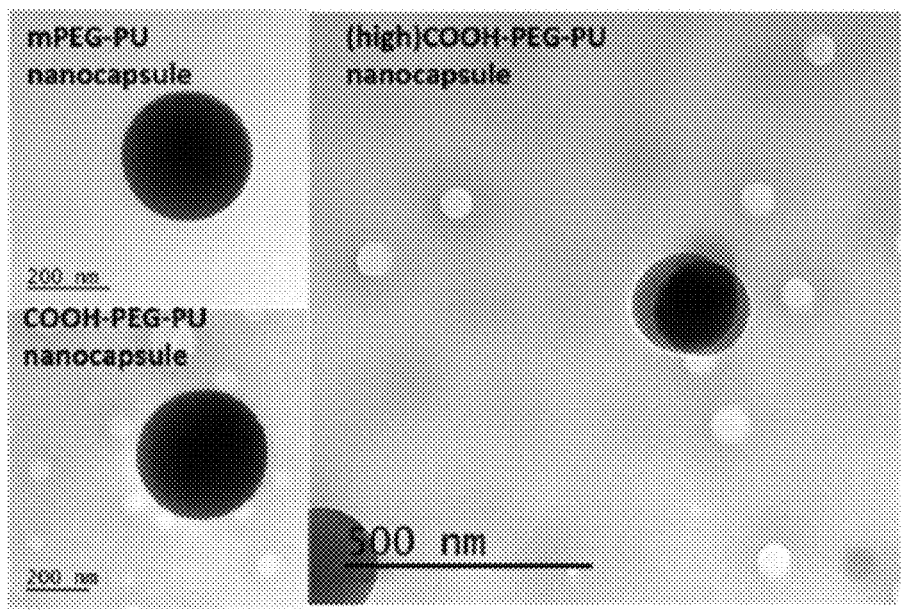
FIGURE 2C

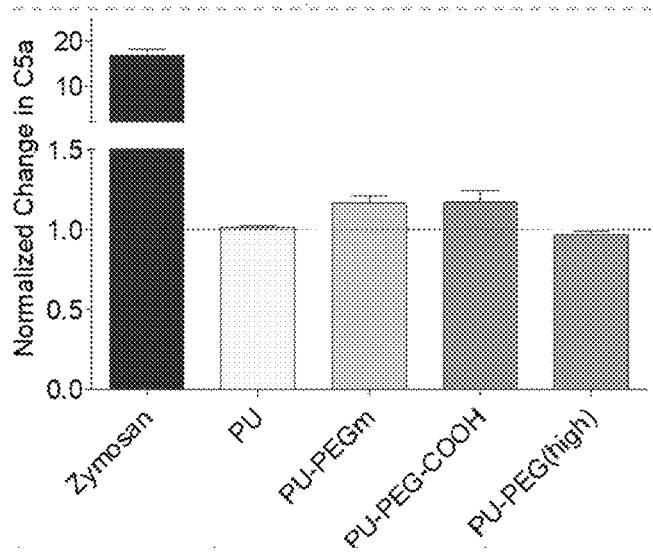
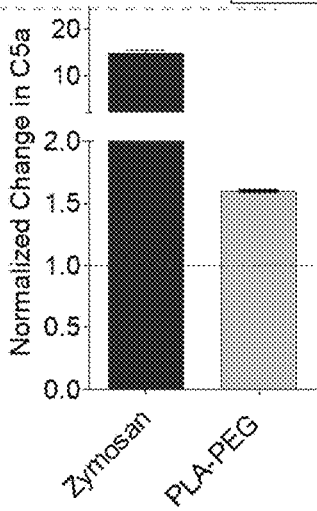
FIGURE 3B
FIGURE 3C
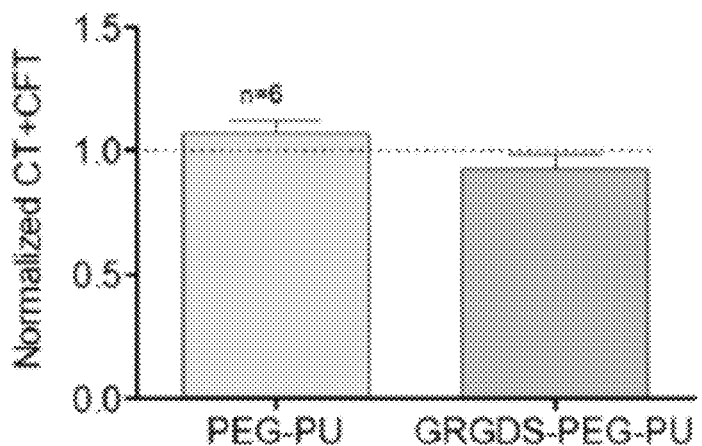
FIGURE 4A

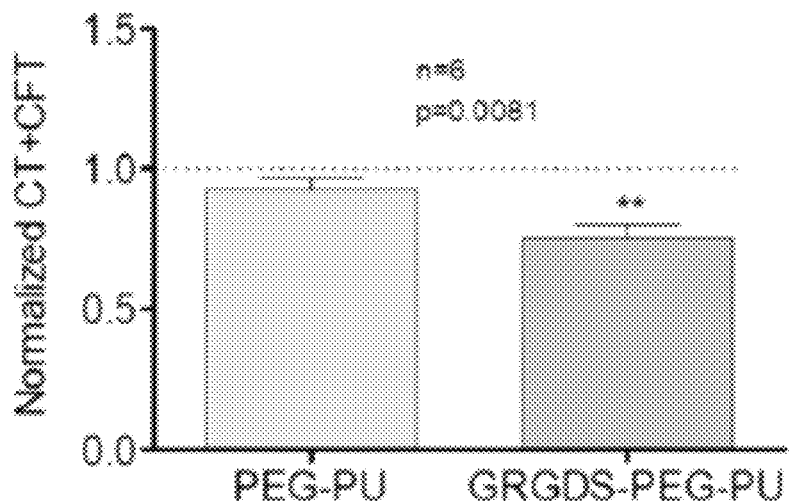
FIGURE 4B
| | Control nanocapsules | Hemostatic nanocapsules |
|---|---|---|
| Size (nm) | 147.9±8.53 | 216±57.68 |
| Moles of PEG/ Moles of IPDI | | 1 mol PEG/83 moles of IPDI |
| Peptide density | | 35.55 ug GRGDS/mg nanocapsules |
FIGURE 4C
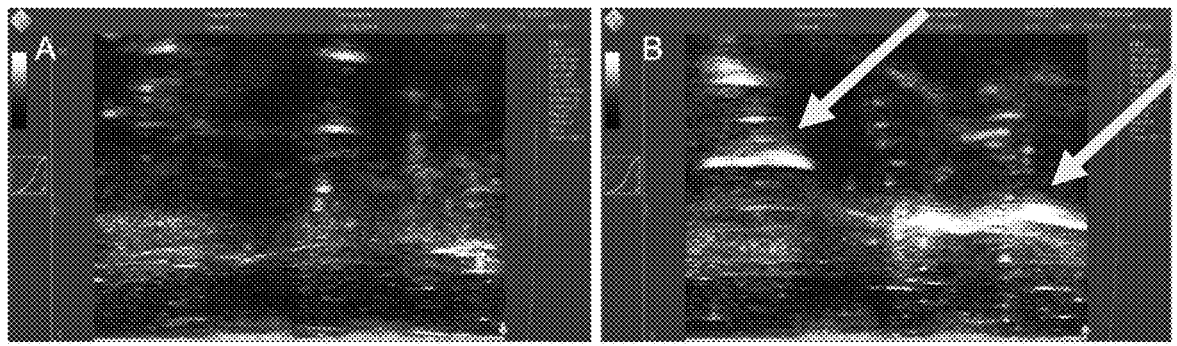
FIGURE 5A  FIGURE 5B

Hemostatic Nanocapsules and Ultrasound
Nanocapsules are administered intravenously to control bleeding and identify sites of trauma in cojunction with ultrasound

HEMOSTATIC NANOCAPSULES FOR STOPPING BLEEDING, VISUALIZING INJURY, AND DELIVERING DRUGS

CROSS REFERENCE TO RELATED APPLICATIONS

This application claims priority to U.S. Provisional Patent Application No. 63/222,044 filed on Jul. 15, 2021 in the name of Erin Lavik et al. and entitled "Hemostatic Nanocapsules for Stopping Bleeding, Visualizing Injury, and Delivering Drugs," which is hereby incorporated by reference herein in its entirety.

STATEMENT REGARDING FEDERALLY SPONSORED RESEARCH

This invention was made with government support under W81XWH-18-2-0061 awarded by the United States Army Medical Research Acquisition Activity. The government has certain rights in the invention.

FIELD

The present invention relates to PEGylated polyurethane nanocapsules, wherein the PEGylated polyurethane nanocapsules can further comprise at least one peptide motif, at least one encapsulated molecule, or both. The presence of the at least one peptide motif makes the PEGylated polyurethane nanocapsules hemostatic and capable of evading complement-mediated initial infusion reactions.

Advantageously, the PEGylated polyurethane nanocapsules can be triggered to deliver the encapsulated molecule, if present, using noninvasive ultrasound energy.

BACKGROUND

With almost 30 to 40% of trauma mortality due to blood loss, and 33 to 56% of this percentage occurring during the prehospital period, trauma is a leading cause of death, especially for ages under 46 [1]. While there are treatments for external and peripheral bleeding, there are no treatments that can be deployed in the field to control internal bleeding. The time immediately following trauma is critical, as, in case of blunt trauma, the 'golden hour' could be utilized for a positive impact to improve survival chances [2, 3]. Controlling hemorrhaging is the first step in managing casualties. An immediate on-field response can provide the scope of controlling exsanguination and saving lives by prolonging the time to move and stabilize the patient following catastrophic trauma incidents. While first responders can play a role in controlling external bleeding through pressure, in the case of internal bleeding, the application of intravenous hemostats is not possible until a medical facility is reached. The hemostatic nanoparticles are designed to mimic the role of fibrinogen consisting of a polymeric core, with poly(ethylene glycol) corona, with a peptide sequence GRGDS conjugated to it. The peptide motif binds with glycoprotein IIb/IIIa in the activated platelets and helps in forming clots faster to reduce bleeding [4, 5]. The nanoparticles effectively reduce bleeding and improve survival significantly in small animal models [5], and these can mitigate internal bleeding and improve the pathologic outcomes after traumatic brain injuries following blast trauma in small animals [6]. Disadvantageously, the nanoparticles are known to trigger the complement system in large animal trauma models even at very low dosages [7].

The complement system is the first-in-line defense of the immune system against pathogens, and it is active at all times, controlled by several complement regulators. Uninhibited complement activation may eventually lead to inflammatory responses as severe as anaphylaxis, an acute life-threatening respiratory failure [8]. As the complement system attacks all components that are not recognized as healthy or familiar, nanomedicines such as the hemostatic nanoparticles may elicit complement-mediated initial infusion reactions as well. Such immune responses lead to vasodilation, increased tissue permeability, edema, and a drastic fall in blood pressure leading to shock, and symptoms appear within minutes after exposure to an allergen [9, 10]. While it is more reproducibly present in porcine animals, the complement-mediated response is observed in 7% of humans, with a 0.3% chance of fatality [11].

One of the earliest cases of compliment mediated response was due to the liposomal formulation Doxil, an FDA approved PEGylated liposomal formulation of Doxorubicin, a chemotherapy drug for treating several types of malignancies [12]. Slower infusion rates and premedication with antihistamines and glucocorticoids, as well as repeated administration, can control the hypersensitivity reaction but not prevent it entirely [12]. The reaction itself leads to significant morbidity, increased healthcare costs, as well as the inability to take the nanoparticles, because of the adverse reactions, despite the better therapeutic effects in highly sensitive patients [12]. The symptoms of the complement response include increase in heart rate, hypotension, flushing of the skin (erythema), decreased cardiac output, decreased pulmonary pressures, and decreased blood gas levels.

Polyurethane (PU) nanocapsules have the potential of being used as dental resins and bone cement encapsulating self-healing components [15]. The material properties and nanoparticle systems can be modified for controlled release triggered enzymatically [16], leveraging thermo-sensitivity [17] or through pH [18], among many other probable stimuli. Polyurethane nanocapsules formed from macromers of Isophorone diisocyanate (IPDI) and 1,6 hexanediol can be used to encapsulate therapeutics that are released on demand through sonication, most likely due to cavitation [19]. Moreover, polyurethanes, especially with further surface modifications, impart biocompatibility [20] and hemocompatibility [21], making them suitable prospects for the core material of nanoparticles intravenously administered.

There is a continuing need for a non-complement triggering nanoparticle system for effectively transferring a hemostatic nanoparticle to large animal trauma models and to the clinic. This nanoparticle system can be used to improve survival following trauma by controlling bleeding.

SUMMARY

In one aspect, PEGylated polyurethane nanocapsules are described comprising a substantially spherical shell of polyurethane surrounding a core, wherein a surface of the shell of polyurethane is substantially PEGylated.

In another aspect, PEGylated polyurethane nanocapsules are described comprising a substantially spherical shell of polyurethane surrounding a core, wherein a surface of the shell of polyurethane is substantially PEGylated, and wherein the shell comprising the polyurethane further comprises at least one encapsulated molecule.

In still another aspect, PEGylated polyurethane nanocapsules are described comprising a substantially spherical shell of polyurethane surrounding a core, wherein a surface of the shell of polyurethane is substantially PEGylated, and wherein peptide motifs are conjugated to a carboxyl end group of a PEG group.

In yet another aspect, PEGylated polyurethane nanocapsules are described comprising a substantially spherical shell of polyurethane surrounding a core, wherein a surface of the shell of polyurethane is substantially PEGylated, wherein peptide motifs are conjugated to a carboxyl end group of a PEG group, and wherein the shell comprising the polyurethane further comprises at least one encapsulated molecule.

In another aspect, a method of making PEGylated polyurethane nanocapsules is described, said method comprising:
  dissolving surfactant in water and hexadecane to form a mixture;
  stirring or sonicating the mixture at temperature in a range from about 35-45° C.;
  adding isophorone diisocyanate (IPDI), and optionally at least one additional compound to be encapsulated, to the stirred mixture comprising the water, surfactant, and hexadecane to form a solution; sonicating the solution to form an emulsion;
  adding a hydroxy-containing compound to the emulsion, with continued sonication; and reacting the IPDI and the hydroxy-containing compound, with stirring, to form the polyurethane nanocapsules encapsulating the at least one molecule, and adding xPEG-OH to the polyurethane nanocapsules.

In yet another aspect, a method of making PEGylated polyurethane nanocapsules is described, said method comprising:
  dissolving surfactant in water and hexadecane to form a mixture;
  stirring or sonicating the mixture at temperature in a range from about 35-45° C.;
  adding isophorone diisocyanate (IPDI), and optionally at least one additional compound to be encapsulated, to the stirred mixture comprising the water, surfactant, and hexadecane to form a solution; sonicating the solution to form an emulsion;
  adding a hydroxy-containing compound to the emulsion, with continued sonication; and reacting the IPDI and the hydroxy-containing compound, with stirring, to form the polyurethane nanocapsules encapsulating the at least one molecule,
  adding xPEG-OH to the polyurethane nanocapsules, and
  further comprising conjugating a peptide motif to a carboxyl end of a PEG groups using NHS (N-hydroxy succinimide)/EDC (1-Ethyl-3-(3-dimethylaminopropyl) carbodiimide) bioconjugation.

In still another aspect, a method of detecting traumatic bleeding and promoting clotting in a patient that may have experienced trauma is described, said method comprising:
  administering a bolus of PEGylated polyurethane nanocapsules to the patient; and
  scanning the patient using ultrasound to visualize the PEGylated polyurethane nanocapsules in vivo, wherein the PEGylated polyurethane nanocapsules promote clotting at the site of the traumatic bleeding, wherein the PEGylated polyurethane nanocapsules comprise a substantially spherical shell of polyurethane surrounding a core, wherein a surface of the shell of polyurethane is substantially PEGylated.

In another aspect, a method of detecting traumatic bleeding and promoting clotting in a patient that may have experienced trauma is described, said method comprising:
  administering a bolus of PEGylated polyurethane nanocapsules to the patient; and
  scanning the patient using ultrasound to visualize the PEGylated polyurethane nanocapsules in vivo, wherein the PEGylated polyurethane nanocapsules promote clotting at the site of the traumatic bleeding, wherein the PEGylated polyurethane nanocapsules comprise a substantially spherical shell of polyurethane surrounding a core, wherein a surface of the shell of polyurethane is substantially PEGylated, and wherein the shell comprising the polyurethane further comprises at least one encapsulated molecule.

In yet another aspect, a method of detecting traumatic bleeding and promoting clotting in a patient that may have experienced trauma is described, said method comprising:
  administering a bolus of PEGylated polyurethane nanocapsules to the patient; and
  scanning the patient using ultrasound to visualize the PEGylated polyurethane nanocapsules in vivo, wherein the PEGylated polyurethane nanocapsules promote clotting at the site of the traumatic bleeding, wherein the PEGylated polyurethane nanocapsules comprise a substantially spherical shell of polyurethane surrounding a core, wherein a surface of the shell of polyurethane is substantially PEGylated, and wherein peptide motifs are conjugated to a carboxyl end group of a PEG group.

In still another aspect, a method of detecting traumatic bleeding and promoting clotting in a patient that may have experienced trauma is described, said method comprising:
  administering a bolus of PEGylated polyurethane nanocapsules to the patient; and
  scanning the patient using ultrasound to visualize the PEGylated polyurethane nanocapsules in vivo, wherein the PEGylated polyurethane nanocapsules promote clotting at the site of the traumatic bleeding, wherein the PEGylated polyurethane nanocapsules comprise a substantially spherical shell of polyurethane surrounding a core, wherein a surface of the shell of polyurethane is substantially PEGylated, wherein peptide motifs are conjugated to a carboxyl end group of a PEG group, and wherein peptide motifs are conjugated to a carboxyl end group of a PEG group.

In another aspect, a method of detecting traumatic bleeding in a patient that may have experienced trauma and releasing an anticoagulant to the detected traumatic bleeding is described, said method comprising:
  administering a bolus of PEGylated polyurethane nanocapsules to a patient that may have experienced trauma;
  scanning the patient using ultrasound to visualize the PEGylated polyurethane nanocapsules in vivo to detect traumatic bleeding; and
  applying ultrasound energy in proximity of the traumatic bleeding to release an amount of anticoagulant from the PEGylated polyurethane nanocapsules to the detected traumatic bleeding, wherein the PEGylated polyurethane nanocapsules comprise a substantially spherical shell of polyurethane surrounding a core, wherein a surface of the shell of polyurethane is substantially PEGylated, and wherein the shell comprising the polyurethane further comprises at least one encapsulated anticoagulant.

In yet another aspect, a method of detecting traumatic bleeding in a patient that may have experienced trauma and releasing an anticoagulant to the detected traumatic bleeding is described, said method comprising:

administering a bolus of PEGylated polyurethane nanocapsules to a patient that may have experienced trauma;

scanning the patient using ultrasound to visualize the PEGylated polyurethane nanocapsules in vivo to detect traumatic bleeding; and applying ultrasound energy in proximity of the traumatic bleeding to release an amount of anticoagulant from the PEGylated polyurethane nanocapsules to the detected traumatic bleeding, wherein the PEGylated polyurethane nanocapsules comprise a substantially spherical shell of polyurethane surrounding a core, wherein a surface of the shell of polyurethane is substantially PEGylated, wherein peptide motifs are conjugated to a carboxyl end group of a PEG group, and wherein the shell comprising the polyurethane further comprises at least one encapsulated anticoagulant.

Other aspects, features and embodiments of the invention will be more fully apparent from the ensuing disclosure and appended claims.

BRIEF DESCRIPTION OF THE FIGURES

FIG. 2A: Schematic representation of polyurethane nanocapsules with and without PEGylation.

FIG. 2B: A summary of the size and surface charge of the PEGylated and non-PEGylated nanocapsules from DLS. The presence of PEG was confirmed through 1H-NMR in deuterated water.

FIG. 2C: TEM images of the PEGylated polyurethane nanocapsules confirm the size observed through DLS.

FIG. 3A: Quantifying complement protein in vitro for polyurethane nanocapsules. The nanocapsules were incubated with complement protected human serum and incubated for 45 minutes at 37° C.

FIG. 3B: Complement activation assay for C5a in vitro. Importantly, the polyurethane nanoparticles and subsequent modifications do not activate complement. The complement protein C5a was least for the non-PEGylated nanocapsules and the highly PEGylated nanocapsules.

FIG. 3C: Change in complement protein C5a for poly (lactic acid) nanoparticles. Even highly PEGylated poly (lactic acid) nanoparticles lead to a greater change in complement protein C5a than the PEGylated and non-PEGylated polyurethane nanocapsules.

FIG. 4A: Evaluating the impact on coagulation in vitro. The clotting time, relative to the control nanocapsules (PEG-PU) or saline (dotted line), was lower for the hemostatic nanocapsules at 2.5 mg/ml concentration but not significantly different.

FIG. 4B. Evaluating the impact on coagulation in vitro. The clotting time, relative to the control nanocapsules (PEG-PU) or saline (dotted line), was the least for the hemostatic nanocapsules at 5 mg/ml concentration and significantly different as evaluated using t-test.

FIG. 4C: A summary of the control nanocapsules relative to the hemostatic nanocapsules.

FIG. 5A: Rat liver, ex vivo imaged via ultrasound.

FIG. 5B: Rat liver, ex vivo with hemostatic nanocapsules, imaged via ultrasound. The areas of very bright signal are collections of nanocapsules in the liver.

DETAILED DESCRIPTION, AND PREFERRED EMBODIMENTS THEREOF

Figure 1A:
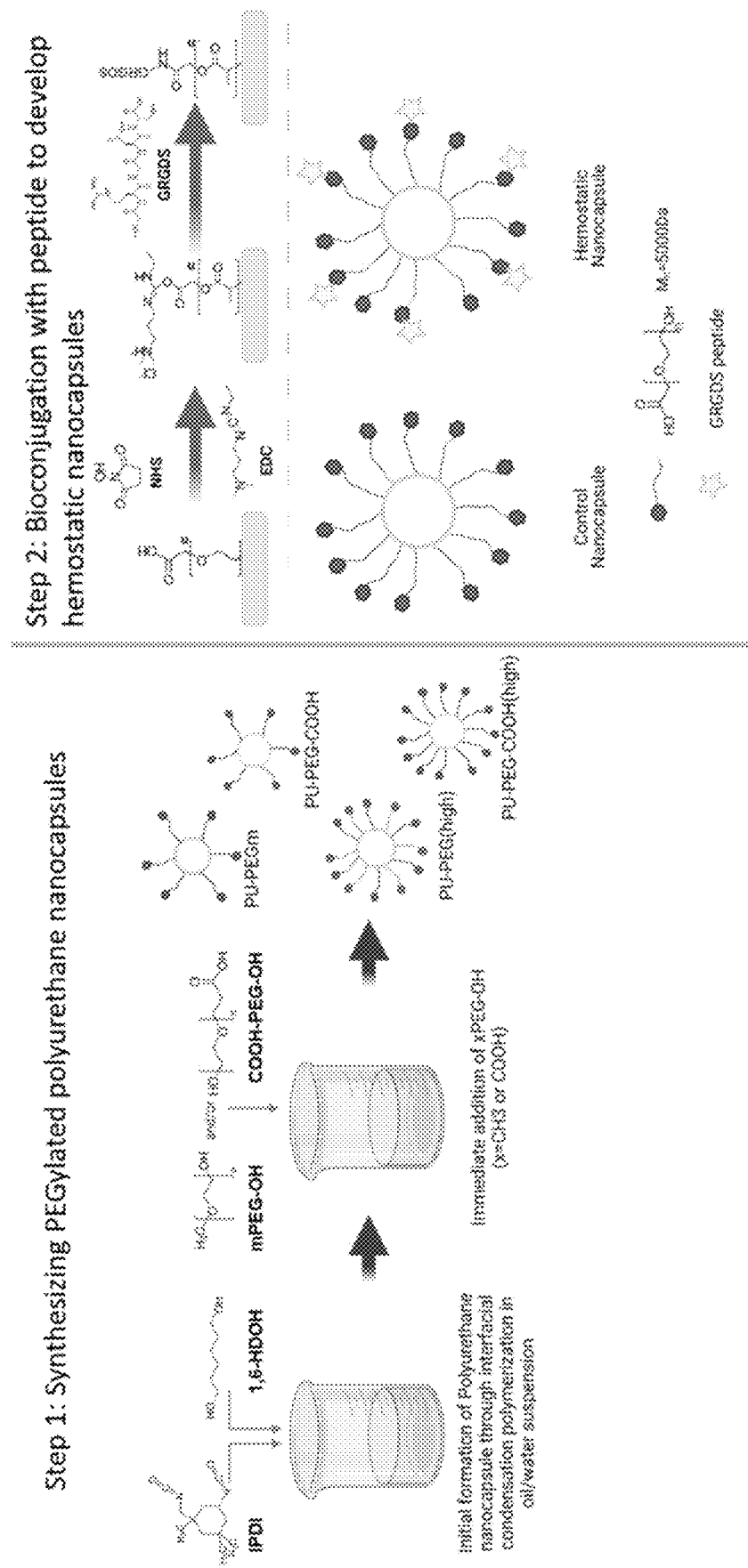
FIG. 1A: Synthesizing PEGylated polyurethane nanocapsules and consequent bioconjugation to prepare hemostatic nanocapsules. In the first step, polyurethane nanocapsules are synthesized through interfacial condensation polymerization between Isophorone diisocyanate (IPDI) in the oil phase and 1,6 hexanediol (1,6 HDOH) in the aqueous phase. Immediately adding poly(ethylene glycol) with hydroxyl end group allows conjugation of PEG chain to the surface. In the second step, hemostatic nanocapsules are prepared by utilizing NHS/EDC zero-length linkers; peptide motif GRGDS is conjugated to the carboxyl end groups present in the PEG chains.

Although the claimed subject matter will be described in terms of certain embodiments, other embodiments, including embodiments that do not provide all of the benefits and features set forth herein, are within the scope of this disclosure as well. Various structural and parameter changes may be made without departing from the scope of this disclosure.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents, and other references mentioned herein are incorporated by reference in their entirety. The materials, methods, and examples disclosed herein are illustrative only and not intended to be limiting.

"About" and "approximately" are used to provide flexibility to a numerical range endpoint by providing that a given value may be "slightly above" or "slightly below" the endpoint without affecting the desired result, for example, +/−5%.

The phrase "in one embodiment" or "in some embodiments" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

As defined herein, "substantially PEGylated" corresponds to a high density PEGylation of the polyurethane nanocapsules having a mole poly(ethylene glycol) (PEG) (cumulative) to mole IPDI ratio of about 1:80 to about 1:750, preferably about 1:80 to about 1:500, and even more preferably from about 1:100 to about 1:300.

As defined herein, "encapsulated" in the polyurethane nanocapsule can include at least one of: exposure of the at least one molecule on an outside surface of the shell, exposure of the at least one molecule on an inside surface of the shell, or the at least one molecule is contained within the polyurethane shell between the outside surface and the inside surface, or any combination thereof.

As defined herein, "substantially spherical" corresponds to a spherical or nearly-spherical nanocapsule. In some embodiments, the substantially spherical nanocapsule can have an average nanocapsule aspect ratio less than about 1.5. In further embodiments, the average nanocapsule aspect ratio can be less than about 1.1. As used herein, "aspect ratio" refers to the longest dimension of a nanocapsule divided by the shortest dimension of the nanocapsule. It should be appreciated by the person skilled in the art that the substantially spherical nanocapsules may look deflated following lyophilization. Further, substantially spherical allows for some flat or irregular surfaces along interface contact points.

As used herein, the term "nanocapsules" can be used interchangeably with polyurethane nanocapsules and PEGylated polyurethane nanocapsules.

As defined herein, "trauma" includes, but are not limited to, disseminated intravascular coagulation (DIC), trauma-induced coagulopathy (TIC), traumatic brain injury (TBI), and other blunt force internal injuries that may have caused internal bleeding in the patient.

As defined herein, "an antibiotic" include known agents that are capable of killing or attenuating the growth of microorganisms, for example natural and synthetic penicillins and cephalosporins, sulphonamides, erythromycin, kanomycin, tetracycline, chloramphenicol, rifampicin and including gentamicin, ampicillin, benzypenicillin, benethamine penicillin, benzathine penicillin, phenethicillin, phenoxy-methyl penicillin, procaine penicillin, cloxacillin, flucloxacillin, methicillin sodium, amoxicillin, bacampicillin hydrochloride, ciclacillin, mezlocillin, pivampicillin, talampicillin hydrochloride, carfecillin sodium, piperacillin, ticarcillin, mecillinam, pirmecillinan, cefaclor, cefadroxil, cefotaxime, cefoxitin, cefsulodin sodium, ceftazidime, ceftizoxime, cefuroxime, cephalexin, cephalothin, cephamandole, cephazolin, cephradine, latamoxef disodium, aztreonam, chlortetracycline hydrochloride, clomocycline sodium, demeclocydine hydrochloride, doxycycline, lymecycline, minocycline, oxytetracycline, amikacin, framycetin sulphate, neomycin sulphate, netilmicin, tobramycin, colistin, sodium fusidate, polymyxin B sulphate, spectinomycin, vancomycin, calcium sulphaloxate, sulfametopyrazine, sulphadiazine, sulphadimidine, sulphaguanidine, sulphaurea, capreomycin, metronidazole, tinidazole, cinoxacin, ciprofloxacin, nitrofurantoin, hexamine, streptomycin, carbenicillin, colistimethate, polymyxin B, furazolidone, nalidixic acid, trimethoprim-sulfamethoxazole, clindamycin, lincomycin, cycloserine, isoniazid, ethambutol, ethionamide, pyrazinamide and the like; antifungal agents, for example miconazole, ketoconazole, itraconazole, fluconazole, amphotericin, flucytosine, griseofulvin, natamycin, nystatin, and the like; and anti-viral agents such as acyclovir, AZT, ddl, amantadine hydrochloride, inosine pranobex, vidarabine, and the like.

As defined herein, an anti-inflammatory agent includes, but is not limited to, diclofenac, meloxicam, oxaprozin, nabumetone, indomethacin, ibuprofen, ketoprofen, ketorolac, naproxen, celecoxib, felbinac, lornoxicam, mesalazine, triflusal, tinoridine, iguratimod, pamicogrel, etoricoxib, piroxicam, ampiroxicam, cinnoxicam, celecoxib, lumiracoxib, zaltoprofen, lornoxicam, beclometasone, budesonide, ciclesonide, fluticasone, etiprednol, mometasone, montelukast, zileuton, ibudilast, zafirlukast, pranlukast, amelubant, tipelukast, aspirin, and the like.

As defined herein, an "antioxidant" includes, but is not limited to, glutathione, vitamin E, zinc and zinc salts of EDTA.

Ranges of values for chemical concentrations, flow rates, operating temperatures and currents are disclosed herein. The ranges set out a lower limit value and upper limit value. Unless otherwise stated, the ranges include all values to the magnitude of the smallest value (either lower limit values or upper limit value) and ranges between the values of the stated range.

PEGylated Polyurethane Nanocapsules

In a first aspect, a PEGylated polyurethane-based nanocapsule system is described, wherein the nanocapsule system acts as a hemostatic nanomaterial while evading complement-mediated initial infusion reaction. In some embodiments, the PEGylated polyurethane nanocapsules further comprise peptide motifs of interest conjugated to the PEG groups. In some embodiments, these nanocapsules can encapsulate therapeutics for targeted release using stimuli.

In some embodiments, PEGylated polyurethane nanocapsules comprise a substantially spherical shell of polyurethane surrounding a core, wherein a surface of the shell of polyurethane is substantially PEGylated. In some embodiments, the core comprises air. In some embodiments, the core comprises at least one of a solution comprising at least one drug, a solution comprising at least one contrast agent, or a solution comprising at least one fluorinated compound that makes the system more ultrasound responsive. In some embodiments, the core is substantially devoid of triethylene glycol dimethyacrylate (TEGDMA). In some embodiments, the surface of the shell of polyurethane that is substantially PEGylated is the outside surface, i.e., the surface having a larger generalized circumference. In some embodiments, PEGylation groups comprise substantially the same PEG group, e.g., carboxyl-PEG or methoxy-PEG. In some embodiments, PEGylation groups comprise mixtures of two or more PEG groups, for example a mixture of carboxyl-PEG and methoxy-PEG at a ratio from almost fully carboxylated to almost fully methoxylated, e.g., greater than about 100:1 to about 50:1, about 50:1 to about 25:1, about 25:1 to about 10:1, about 10:1 to about 1:1, about 5:1 to about 1:1, about 2:1 to about 1:1, about 3:2 to about 1:1.5, about 6:5 to about 5:6, about 1:1, about 1:1 to about 1:2, about 2:1 to about 1:2, about 1:1 to about 1:5, about 1:1 to about 1:10, about 1:10 to about 1:25, about 1:25 to about 1:50, about 1:50 to less than 1:100.

In some embodiments, PEGylated polyurethane nanocapsules comprise a substantially spherical shell of polyurethane surrounding a core, wherein a surface of the shell of polyurethane is substantially PEGylated, and wherein the shell comprising the polyurethane further comprises at least one encapsulated molecule. In some embodiments, the core comprises air. In some embodiments, the core is substantially devoid of triethylene glycol dimethyacrylate (TEGDMA). In some embodiments, the surface of the shell of polyurethane that is substantially PEGylated is the outside surface, i.e., the surface having a larger generalized circumference. In some embodiments, PEGylation groups comprise substantially the same PEG group, e.g., carboxyl-PEG or methoxy-PEG. In some embodiments, PEGylation groups comprise mixtures of two or more PEG groups, for example a mixture of carboxyl-PEG and methoxy-PEG from almost fully carboxylated to almost fully methoxylated, e.g., greater than about 100:1 to about 50:1, about 50:1 to about 25:1, about 25:1 to about 10:1, about 10:1 to about 1:1, about 5:1 to about 1:1, about 2:1 to about 1:1, about 3:2 to about 2:3, about 6:5 to about 5:6, about 1:1, about 1:1 to about 1:2, about 2:1 to about 1:2, about 1:1 to about 1:5, about 1:1 to about 1:10, about 1:10 to about 1:25, about 1:25 to about 1:50, about 1:50 to less than 1:100. In some embodiments, the at least one encapsulated molecule comprises an anticoagulant. In some embodiments, the at least one encapsulated molecule comprises at least one of TEMPOL, pirfenidone, an anticoagulant, an anti-inflammatory drug, an antibiotic, and/or an antioxidant. In some embodiments, the at least one encapsulated molecule comprises heparin, tissue type Plasminogen Activator (tPA), or argatroban. The at least one molecule can be homogeneously or heterogeneously distributed throughout the substantially spherical shell of polyurethane.

In some embodiments, hemostatic PEGylated polyurethane nanocapsules comprise a substantially spherical shell of polyurethane surrounding a core, and wherein a surface of the shell of polyurethane is substantially PEGylated, and wherein peptide motifs are conjugated to a carboxyl end group of a PEG group. In some embodiments, the core comprises air. In some embodiments, the core is substantially devoid of triethylene glycol dimethyacrylate (TEGDMA). In some embodiments, the surface of the shell of polyurethane that is substantially PEGylated is the outside surface, i.e., the surface having a larger generalized circumference. In some embodiments, PEGylation groups comprise substantially the same PEG group, e.g., carboxyl-PEG or methoxy-PEG. In some embodiments, PEGylation groups comprise mixtures of two or more PEG groups, for example a mixture of carboxyl-PEG and methoxy-PEG from almost fully carboxylated to almost fully methoxylated, e.g., greater than about 100:1 to about 50:1, about 50:1 to about 25:1, about 25:1 to about 10:1, about 10:1 to about 1:1, about 5:1 to about 1:1, about 2:1 to about 1:1, about 3:2 to about 2:3, about 6:5 to about 5:6, about 1:1, about 1:1 to about 1:2, about 2:1 to about 1:2, about 1:1 to about 1:5, about 1:1 to about 1:10, about 1:10 to about 1:25, about 1:25 to about 1:50, about 1:50 to less than 1:100. In some embodiments, the peptide motifs comprise a targeting peptide comprising an amine such as a RGD peptide including, but not limited to, GRGDS. In some embodiment, the peptide motifs comprise cRGD DNA aptamers to receptors on cells. In some embodiments, the substantially PEGylated nanocapsules are conjugated with the peptide motifs using NHS (N-hydroxy succinimide)/EDC (1-Ethyl-3-(3-dimethylaminopropyl) carbodiimide) bioconjugation wherein the peptide motifs are attached to the PEG via an amide linkage. In some embodiments, the percentage of PEG groups conjugated with peptide motifs is in a range from about 5% to about 95%, for example, a range of about 5% to about 25%, or a range of about 5% to about 50%, or a range of about 25% to about 75%, or a range of about 50% to about 75%, or a range of about 75% to about 95%, or a range of about 40% to about 60%, or a range of about 45% to about 55%, to achieve a peptide density on the nanocapsules of about 10 µg per mg of nanocapsules to about 50 µg per mg of nanocapsules.

In some embodiments, hemostatic PEGylated polyurethane nanocapsules comprise a substantially spherical shell of polyurethane surrounding a core, wherein a surface of the shell of polyurethane is substantially PEGylated, wherein peptide motifs are conjugated to a carboxyl end group of a PEG group, and wherein the shell comprising the polyurethane further comprises at least one encapsulated molecule. In some embodiments, the core comprises air. In some embodiments, the core is substantially devoid of triethylene glycol dimethyacrylate (TEGDMA). In some embodiments, the surface of the shell of polyurethane that is substantially PEGylated is the outside surface, i.e., the surface having a larger generalized circumference. In some embodiments, PEGylation groups comprise substantially the same PEG group, e.g., carboxyl-PEG or methoxy-PEG. In some embodiments, PEGylation groups comprise mixtures of two or more PEG groups, for example a mixture of carboxyl-PEG and methoxy-PEG from almost fully carboxylated to almost fully methoxylated, e.g., greater than about 100:1 to about 50:1, about 50:1 to about 25:1, about 25:1 to about 10:1, about 10:1 to about 1:1, about 5:1 to about 1:1, about 2:1 to about 1:1, about 3:2 to about 2:3, about 6:5 to about 5:6, about 1:1, about 1:1 to about 1:2, about 2:1 to about 1:2, about 1:1 to about 1:5, about 1:1 to about 1:10, about 1:10 to about 1:25, about 1:25 to about 1:50, about 1:50 to less than 1:100. In some embodiments, the peptide motifs comprise a targeting peptide comprising an amine such as a RGD peptide including, but not limited to, GRGDS. In some embodiments, the substantially PEGylated nanocapsules are conjugated with the peptide motifs using NHS/EDC bioconjugation wherein the peptide motifs are attached to the PEG via an amide linkage. In some embodiments, the percentage of PEG groups conjugated with peptide motifs is in a range from about 5% to about 95%, for example, a range of about 5% to about 25%, or a range of about 5% to about 50%, or a range of about 25% to about 75%, or a range of about 50% to about 75%, or a range of about 75% to about 95%, or a range of about 40% to about 60%, or a range of about 45% to about 55%, to achieve a peptide density on the nanocapsules of about 10 μg per mg of nanocapsules to about 50 μg per mg of nanocapsules. In some embodiments, the at least one encapsulated molecule comprises an anticoagulant. In some embodiments, the at least one encapsulated molecule comprises at least one of TEMPOL, pirfenidone, an anticoagulant, an anti-inflammatory drug, an antibiotic, and/or an antioxidant. In some embodiments, the at least one encapsulated molecule comprises heparin, tissue type Plasminogen Activator (tPA), or argatroban. The at least one molecule can be homogeneously or heterogeneously distributed throughout the substantially spherical shell of polyurethane.

The PEGylated polyurethane nanocapsules and the hemostatic PEGylated polyurethane nanocapsules described herein have an effective mean diameter of about 50 to about 900 nm. The nanocapsules can be tailored to create the optimum size depending on the method of administration, the PEG groups used, the peptide motifs used, the amount of encapsulated molecule loaded and/or released, and the pathology to be treated. Ranges of effective mean diameters contemplated include, but are not limited to, about 50 nm to about 150 nm, about 100 nm to about 200 nm, about 150 nm to about 250 nm, about 150 nm to about 300 nm, about 200 nm to about 300 nm, about 300 nm to about 400 nm, about 400 nm to about 500 nm, about 500 nm to about 600 nm, about 600 nm to about 700 nm, about 700 nm to about 800 nm, about 800 nm to about 900 nm, about 50 nm to about 250 nm, about 250 nm to about 500 nm, about 500 nm to about 750 nm, or about 750 nm to about 900 nm. In some embodiment, the effective mean diameter is about 150-300 nm. The PEGylated polyurethane nanocapsules and the hemostatic PEGylated polyurethane nanocapsules can have narrow size distribution (e.g., in a range of about 50-75 nm) or a wide size distribution (e.g., in a range of about 100-200 nm).

PEGylated polyurethane nanocapsules can be prepared through interfacial polycondensation by modifying an existing method of preparing polyurethane nanocapsules [19]. Broadly, in one embodiment, a surfactant, such as sodium dodecyl sulfate (SDS), is dissolved in water (e.g., DI water) and hexadecane and stirred or sonicated at temperature in a range from about 35-45° C., preferably about 40° C. for approximately one hour. Isophorone diisocyanate (IPDI) is mixed with water, and when present, the at least one encapsulated molecule, and the IPDI mixture is added to a beaker containing the water, surfactant (e.g., SDS), and hexadecane. The solution is sonicated to form the emulsion. 1,6-hexanediol (HDOH), or similar hydroxy-containing compound, is dissolved in water and added to the emulsion with sonication. This results in the initial formation of polyurethane nanocapsules through interfacial condensation polymerization in an oil/water suspension, with or without the at least one encapsulated molecule. Immediately xPEG-OH, wherein x=$CH_3$ or COOH or a mixture of both, is added to the polyurethane nanocapsules. Light exposure is preferably minimized or eliminated. The nanocapsules can be collected by centrifugation and washed with DI water before flash freezing and lyophilization.

Hemostatic PEGylated polyurethane nanocapsules can be prepared by conjugation of peptide motifs to the carboxyl ends of the PEG groups using NHS/EDC bioconjugation. Broadly, the PEGylated polyurethane nanocapsules, suspended in water, are reacted with an aqueous solution of NHS and EDC, to generate an intermediate complex. The nanocapsules are collected by centrifugation to remove unreacted NHS/EDC. The intermediate complex, suspended in water, is reacted with an aqueous solution of the peptide motif, e.g., GRGDS, and the bioconjugation occurs. The nanocapsules can be collected by centrifugation and washed with DI water before flash freezing and lyophilization.

In some embodiments, the PEGylated polyurethane nanocapsules described herein stored for long periods of time, and resuspended just prior to use, although it should be appreciated by the person skilled in the art that the nanocapsules can be used immediately following synthesis, i.e., without being lyophilized. Being able to lyophilize, store, and resuspend nanocapsules increased their ability to be deployed and used in a number of environments and applications. Further, the PEGylated polyurethane nanocapsules are biocompatible and biodegradable.

In some embodiments, the hemostatic PEGylated polyurethane nanocapsules described herein stored for long periods of time, and resuspended just prior to use, although it should be appreciated by the person skilled in the art that the nanocapsules can be used immediately following synthesis, i.e., without being lyophilized. Being able to lyophilize, store, and resuspend nanocapsules increased their ability to be deployed and used in a number of environments and applications. Further, the hemostatic PEGylated polyurethane nanocapsules are biocompatible and biodegradable.

Advantageously, the PEGylated polyurethane nanocapsules and the hemostatic PEGylated polyurethane nanocapsules described herein can be administered intravenously [13, 14]. Polyurethane nanoparticles have been used intravenously in a number of applications and appear to clear without issue [59]. It should be appreciated by the person skilled in the art that the PEGylated polyurethane nanocapsules and the hemostatic PEGylated polyurethane nanocapsules described herein can be administered via other routes as well including, but not limited to, intravenous, intraarterial, intrathecal, intradermal, intracavitary, oral, rectal, intramuscular, subcutaneous, intracisternal, intravaginal, intraperitonial, intravitreal, suprachoroidal, subconjunctival, topical, buccal, and/or nasal routes of administration. The route of administration may also impact the dosage requirements.

Advantageously, the hemostatic PEGylated polyurethane nanocapsules described herein are not only able to substantially avoid complement-mediated infusion reactions but also able to display effective hemostatic activity (e.g., lower clot formation time).

Methods of Using the PEGylated Polyurethane Nanocapsules

The PEGylated polyurethane nanoparticles described herein may be useful not only for stopping bleeding and improving survival, but in some cases, for reducing the neurological devastation of traumatic brain injury (TBI) [37]. The challenge, though, lies in the fact that in TBI as well as many other traumas, patients rapidly switch between hypercoagulable and hypercoagulable states making a technology that can help stop bleeding a potential liability [38]. These conditions, hereinafter referred to as the "conditions," include disseminated intravascular coagulation (DIC) [38] and trauma induced coagulopathy (TIC) [39, 40] and traumatic brain injury (TBI) [41-43]. These conditions are extremely hard to predict and treat because the treatment in one moment is directly counter to the treatment the next if the patient's state changes. Thus, management is incredibly difficult and mortality is high [38]. The goal is to safely treat patients even in complex traumas where we need to control hemorrhaging while monitoring and lysing inappropriate clots.

Imaging to identify the sites of bleeding and trauma significantly improves interventions and leads to better outcomes. Sonography or ultrasound has been extremely helpful in dictating care and surgical intervention in level I trauma centers. Disadvantageously, sonography has limits on sensitivity and negative sonographic findings do not rule out bleeding or events that require intervention. Contrast enhanced ultrasound increases the sensitivity and diagnostic capacity of ultrasound imaging for trauma, and in some cases contrast enhanced ultrasound is considered comparable to contrast enhanced CT. However, the common contrast agents in ultrasound, namely microbubbles, have the potential to elicit infusion reactions. Infusion reactions can be difficult to manage under normal hospital conditions and extremely challenging in austere conditions especially in the context of trauma.

Recently, the instant inventors developed polyurethane nanocapsules that can be visualized and triggered using ultrasound to release drugs over a wide range of ultrasound energies [58]. These nanocapsules can be visualized with ultrasound, which would allow the healthcare provider to monitor the patient and their clotting state even in low-resource environments.

Hemostatic PEGylated polyurethane nanocapsules based on hollow polyurethane nanocapsules that are substantially PEGylated and comprise a RGD peptide (GRGDS) are disclosed herein. Advantageously, these hemostatic PEGylated polyurethane nanocapsules can be visualized via ultrasound and can reduce coagulation time (see, e.g., FIG. 4B). Without being bound by theory, it is hypothesized that the nanocapsules, due to the flexibility of the polyurethane shells and their air-filled centers, are extremely bright when visualized via ultrasound which has the potential to allow their visualization in a number of tissues. The hemostatic efficacy of these nanocapsules coupled with their ability to be visualized via ultrasound provides the foundation for using them in hemostatic applications.

For example, hemostatic PEGylated polyurethane nanocapsules were administered to rodent livers ex vivo to confirm parameters to facilitate visualization. FIG. 5A shows a liver without the nanocapsules described herein and FIG. 5B shows a liver with the nanocapsules described herein. The nanocapsules appear as bright signals in the image both as dots for small clusters and in areas with large numbers are bright regions. Advantageously, the hemostatic PEGylated polyurethane nanocapsules accumulate in sites of bleeding, and as such, not only are they positioned to help stop bleeding, but they will also allow visualization of the injuries in a non-invasive manner which will help treat people in any environment.

In some embodiments, the hemostatic PEGylated polyurethane nanocapsules described herein can participate in forming clots and augmenting hemostasis, and in the process, they become localized at the injury (e.g., trauma) sites. Because they can be visualized using ultrasound, the primary sites of bleeding and trauma can be located. Handheld ultrasound imaging systems are readily available and suitable for deployment in austere environments associated with prolonged field care.

Accordingly, in a second aspect, a method of detecting traumatic bleeding and promoting clotting in a patient that may have experienced trauma is described, said method comprising administering a bolus of the hemostatic PEGylated polyurethane nanocapsules described herein to the patient, and scanning the patient using ultrasound to visualize the hemostatic PEGylated polyurethane nanocapsules in vivo, wherein the hemostatic PEGylated polyurethane nanocapsules promote clotting at the site of the traumatic bleeding. The hemostatic PEGylated polyurethane nanocapsules will accumulate in sites of traumatic bleeding thereby allowing the healthcare provider to conclude if the patient has experienced trauma and assist in the identification of additional therapies to treat the patient based on the site of traumatic bleeding. Furthermore, the presence of the hemostatic PEGylated polyurethane nanocapsules will allow the healthcare provider to monitor clotting at the site of the traumatic bleeding. In some embodiments, the hemostatic PEGylated polyurethane nanocapsules are administered intravenously, intraarterially, intrathecally, intradermally, intracavitarily, orally, rectally, intramuscularly, subcutaneously, intracisternally, intravaginally, intraperitonially, intravitreally, suprachoroidally, subconjunctivally, topically, buccally, and/or nasally. In some embodiments, the hemostatic PEGylated polyurethane nanocapsules are administered intravenously. In some embodiments, the hemostatic PEGylated polyurethane nanocapsules to be used in the second aspect are described herein in the first aspect. In some embodiments, the bolus of hemostatic PEGylated polyurethane nanocapsules administered is in a range from about 1 mg of hemostatic PEGylated polyurethane nanocapsules per kg of patient (1 mg/kg) to about 10 mg/kg.

Advantageously, ultrasound can be focused non-invasively and at a precise depth with sub-millimeter precision. Ultrasound can readily propagate to distances ranging from tens of cm in the MHz range to several meters in the kHz range. The disclosure contemplates that various ultrasound parameters are utilized in the practice of the methods disclosed herein. Thus, parameters including, but not limited to, frequency, pulse repetition frequency (e.g., from about 1 to about 50 Hz), and the number of cycles (e.g., from about 1 to about 100) per pulse are contemplated for use according to the methods described herein. In some embodiments, the disclosure contemplates that ultrasound frequencies between about 0.25 MHz and about 50 MHz, or from about 2 MHz to about 12 MHz, or from about 25 MHz to about 50 MHz, are useful in the methods disclosed herein to enable visualization of the polyurethane nanocapsules. For example, the ultrasound system can be a high frequency imaging system with a 40 MHz phased array imaging probe or a portable ultrasound imaging system with a 18 MHz linear imaging probe.

It is known that at specific ultrasound pulsing parameters, nanoparticle surface chemistries can be altered including cleaving functionalities [44-47] due to either elevated temperature or mechanical stimuli. Focused ultrasound (FUS) can be used to provide a combination of these controlling stimuli so that after site-specific delivery, the particles can be locally modulated to achieve the desired coagulation response. FUS is a completely non-invasive treatment modality that can remotely modulate tissue temperature or induce mechanical stimuli with high spatial and temporal resolution. FUS pulsing parameters can be tailored to induce either reversible (tissue/cell modulation) [48-51] or irreversible (tissue ablation) bio-effects [52-56]. FUS is an ideal modality for applying thermal and mechanical stimuli to materials in situ with high spatial (millimeter) and temporal (microsecond) precision.

Figure 8:
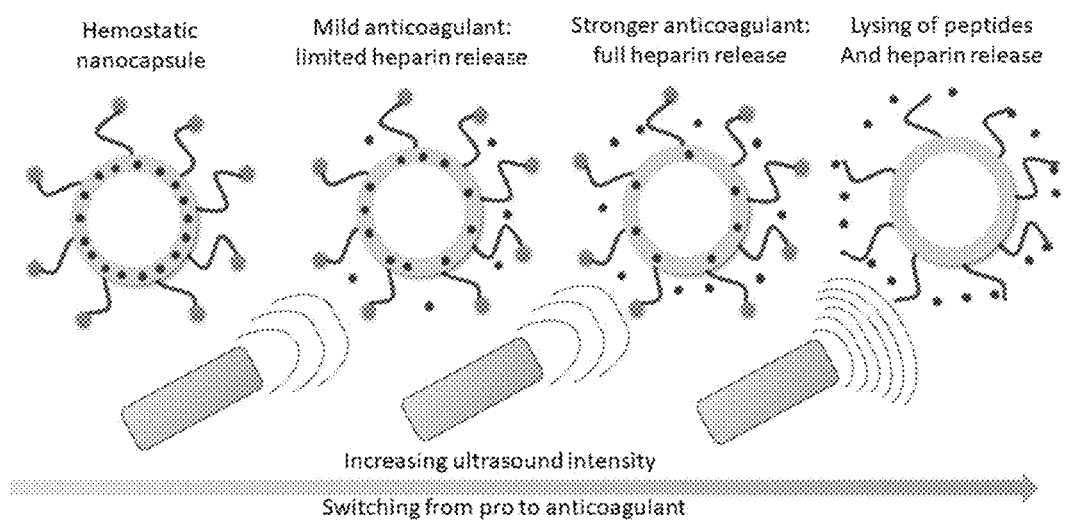
FIG. 8: Schematic of switchable, tunable hemostatic/anticoagulant nanocapsules. As fabricated, the nanocapsules are hemostatic nanoparticles. When exposed to ultrasound, they release an encapsulated anticoagulant and, at higher energies, cleave functional groups and become potential anticoagulant materials.

In some embodiments, the hemostatic PEGylated polyurethane nanocapsules described herein can be loaded with at least one molecule, e.g., an anticoagulant, wherein the inclusion of an anticoagulant creates a hemostatic tool that can be switched using ultrasound energy between pro- and anticoagulant depending on the patient's state. For example, referring to FIG. 8, the polyurethane-based nanocapsules can be triggered using ultrasound, wherein depending on the intensity of the ultrasound, the anticoagulant can be switched from pro-coagulant to anticoagulant. In some embodiments, the intensity of the ultrasound is in a range from about 1 mW/cm$^2$ to about 17 mW/cm$^2$. Advantageously, because the PEGylated polyurethane nanocapsules can be visualized with ultrasound, the patient and their clotting state can be monitored even in low-resource environments. Moreover, in some embodiments, the hemostatic PEGylated polyurethane nanocapsules comprising the anticoagulant can be triggered, e.g., using ultrasound, to release the anticoagulant to impact clotting.

Accordingly, in a third aspect, a method of detecting traumatic bleeding in a patient that may have experienced trauma and releasing an anticoagulant to the detected traumatic bleeding is described, said method comprising administering a bolus of the hemostatic PEGylated polyurethane nanocapsules to a patient that may have experienced trauma, scanning the patient using ultrasound to visualize the hemostatic PEGylated polyurethane nanocapsules in vivo to detect traumatic bleeding, and applying ultrasound energy in proximity of the traumatic bleeding to release an amount of anticoagulant from the hemostatic PEGylated polyurethane nanocapsules to the detected traumatic bleeding. The hemostatic PEGylated polyurethane nanocapsules will accumulate in sites of traumatic bleeding thereby allowing the healthcare provider to conclude if the patient has experienced trauma and exactly where the traumatic bleeding is positioned. In some embodiments, the hemostatic PEGylated polyurethane nanocapsules can be triggered to release the anticoagulant in vivo, wherein the triggering is noninvasive. In some embodiments, the use of ultrasound permits the healthcare provider to switch the anticoagulant from being a procoagulant and an anticoagulant, depending on the patient's state, thereby further impacting clotting in the patient. In some embodiments, the hemostatic PEGylated polyurethane nanocapsules are administered intravenously, intraarterially, intrathecally, intradermally, intracavitarily, orally, rectally, intramuscularly, subcutaneously, intracisternally, intravaginally, intraperitoneally, intravitreally, suprachoroidally, subconjunctivally, topically, buccally, and/or nasally. In some embodiments, the hemostatic PEGylated polyurethane nanocapsules are administered intravenously. In some embodiments, the anticoagulant comprises heparin. In some embodiments, the anticoagulant comprises tissue type Plasminogen Activator (tPA). In some embodiments, the anticoagulant comprises argatroban.

While there have been hemostatic nanoparticle systems and nanoparticle systems that can be triggered via ultrasound to deliver drugs, the combination of the two is a fundamentally new approach that can transform how traumas, brain injuries, strokes, and complications arising from liver disease, cancers, and diabetes are imaged and treated. The system and method of use described herein can stop bleeding and, on demand, can be switched to an anticoagulant state. The system can non-invasively in a tunable manner using ultrasound allow the healthcare provider to monitor the therapy in real time. This approach, based on the nanocapsule technology functionalized with RGD peptides, as described herein, and further loaded with an anticoagulant, e.g., heparin, can control bleeding and has the potential to revolutionize patient care and survival. Because these nanocapsules have hollow cores, they exhibit high contrast via ultrasound imaging. Their functionalization with RGD peptides structurally mimics hemostatic agents (see, Example 1), and the delivery of anticoagulants, e.g., heparin, from nanomaterials has been shown to disrupt clots [57].

The features and advantages of the invention are more fully illustrated by the following non-limiting examples, wherein all parts and percentages are by weight, unless otherwise expressly stated.

Example 1

Materials

For preparing the nanocapsules, monomers Isophorone diisocyanate (IPDI) 98% (ACROS Organics), 1,6-hexanediol (HDOH) 97% (ACROS Organics), surfactant Sodium dodecyl sulfate (SDS) (Fisher Scientific), and co-stabilizer 99% pure hexadecane were used without further purification. For bioconjugation, peptide motif GRGDS was obtained from Selleckchem (Houston, TX). N-hydroxy succinimide (NHS) and 1-Ethyl-3-(3-dimethylaminopropyl) carbodiimide (EDC) were obtained from Sigma Aldrich (Merck KGaA, Darmstadt, Germany).

Developing PEGylated Polyurethane Nanocapsules

PEGylated nanocapsules were prepared through interfacial polycondensation by modifying an existing method of preparing polyurethane nanocapsules [19]. An oil-water emulsion was prepared using 1.1 g SDS dissolved in 70 mL deionized (DI) water and 1.145 mL n-hexadecane. The oil-water emulsion was stirred at 40° C. for 1 hour at 300 rpm. To the oil-water emulsion, 2.094 mL of IPDI mixed with 7 mL DI water was added and stirred. As the IPDI solution entered the pre-emulsification solution, the stirring speed was increased to 400 rpm. The solution was mixed at 400 rpm and 40° C. for 10 minutes. The solution was then sonicated using a 130-Watt Ultrasonic Processor with Thumb-actuated Pulser at an amplitude of 38% to break up any IPDI molecules for 1 minute. While still under sonication, over 40 seconds, an aqueous solution of 5.9 g of HDOH and 10 mL of DI water was added into the system. The reaction mixture was maintained at 40° C. and stirring at 300 rpm. Immediately thereafter, HO-PEG-COOH/HO-mPEG, wherein mPEG is methoxy-PEG, dissolved in DI water was added. The nanocapsules were collected through centrifugation at 10000 rpm for 10 minutes, and then resuspended in DI water. This step was repeated two more times, for a total of three washes. The nanocapsules resuspended in DI water were flash frozen and lyophilized.

When compounds such as anticoagulants are to be encapsulated by the nanocapsules, the compounds are added in the water along with the IPDI component during the interfacial polymerization step.

Characterization of the Nanocapsules

Nanocapsules prepared where characterized to determine the size and zeta-potential using the Malvern ZetaSizer (Nano ZS90). The nanocapsules were resuspended in 190 proof ethanol for sizing. The zeta-potential was determined by resuspending the nanocapsules in 10 mM potassium chloride (KCl). Both the size and zeta potential measurements were run in triplicates Determining Amount of PEG in the Nanocapsules To determine the amount of PEG present, 1H-NMR was used. The nanocapsules were resuspended in deuterated water and the peaks generated were used to calculate the moles of PEG present in the sample.

Conjugating with GRGDS Peptide Motif to Develop Hemostatic Nanocapsules

The PEGylated nanocapsules were conjugated with the GRGDS peptide motif through NHS/EDC bioconjugation. The PEGylated nanocapsules resuspended in DI water were allowed to react with NHS and EDC in DI water, where utilizing the carboxyl end group of the PEG, an intermediate complex is generated. The nanocapsules were collected by centrifugation to discard unreacted NHS and EDC, and then resuspended in DI water again. GRGDS dissolved in DI water was added and through the primary amine of the peptide, bioconjugation takes place. The nanocapsules were then collected through centrifugation, resuspended in DI water and flash frozen to lyophilize.

Quantifying Amount of Peptide Through Ortho-Pthalaldehyde Assay

The amount of peptide conjugated was calculated through an ortho-pthalaldehyde assay. The compound ortho-pthalaldehyde in the presence of mercaptoethanol reacts with primary amines to form a fluorophore that absorbs at 340 nm and emits at 455 nm. The optical densities were measured for blank and peptide conjugated nanocapsules in a fluorescent plate reader (Molecular Devices, SpectraMax M2). Based on the standard curve prepared, the amount of peptide within the samples was determined.

Generating Complement Response In Vitro and Quantification Through Complement Assay The change in complement protein C5a was quantified following previously established protocol [22]. The blood matrix was incubated with nanoparticles suspended in Dulbecco's PBS (without calcium and magnesium). As a positive control, Zymosan was used. The dosage used for the nanoparticles and Zymosan was 0.25 mg/mL in serum. The samples were incubated at 37° C. for 45 minutes and then centrifuged at 4000 g for 5 minutes to separate the nanoparticles. The supernatant was aliquoted into clean tubes and stored on ice until assay was carried out using the C5a ELISA assay duo kit (R&D Systems). The optical density for the samples and standards were measured at a wavelength of 450 nm using SpectraMax M2 Microplate Reader (Molecular Devices LLC) with background correction done using reading obtained at 540 nm. The normalized change was measured by comparing the level of C5a observed in the sample incubated with PBS.

$$\text{Normalized Change} = \frac{\text{Biomarker in sample incubated with Zymosan or nanoparticles}}{\text{Biomarker in sample incubated with PBS}}$$

Evaluating Coagulation In Vitro Using Whole Blood Through Rotational Thromboelastometry To evaluate the coagulation in vitro, rodent blood collected through cardiac puncture was used. Using rotational thromboelastometry (ROTEM), the clotting time and clot formation time, and maximum clot firmness were determined. The groups in this study include: the vehicle (minimum essential media), control nanocapsules and hemostatic nanocapsules. The nanocapsules were resuspended in the minimum essential media, and the dosages investigated were 5 mg/mL and 2.5 mg/mL. The normalized changes were determined based on the values observed for the vehicle control.

Statistical Analysis

Chi-square analysis was used to calculate the p-value within groups for the complement protein C5a. As the expected value, the C5a level for serum incubated with PBS was used. In case of the ROTEM data, t-test was used to determine the p-values between the two groups.

Figure 1B:
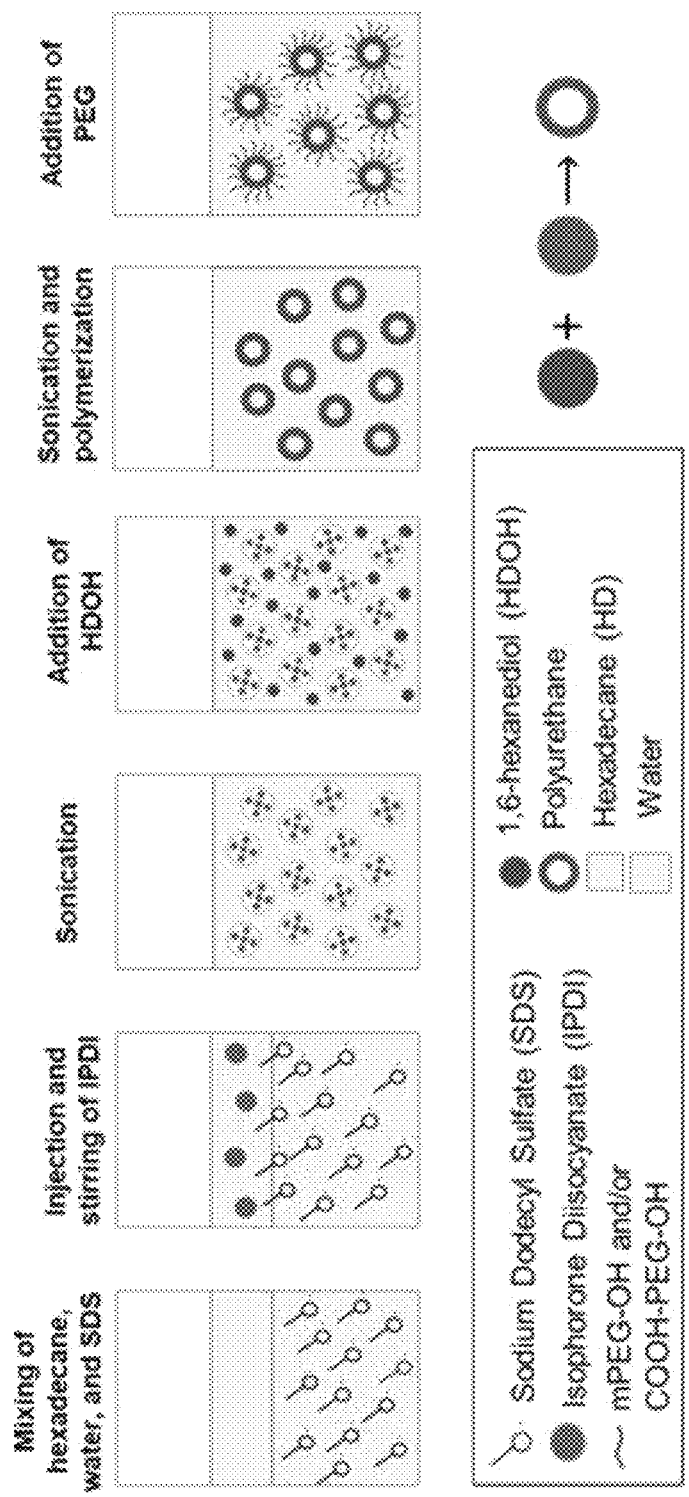
FIG. 1B: Polyurethane nanocapsules are synthesized through interfacial condensation polymerization between IPDI in the oil phase and 1,6 hexanediol (1,6 HDOH) in the aqueous phase. Immediately adding PEG with a hydroxyl end group allows conjugation of the PEG chain to the surface.
Figure 6:
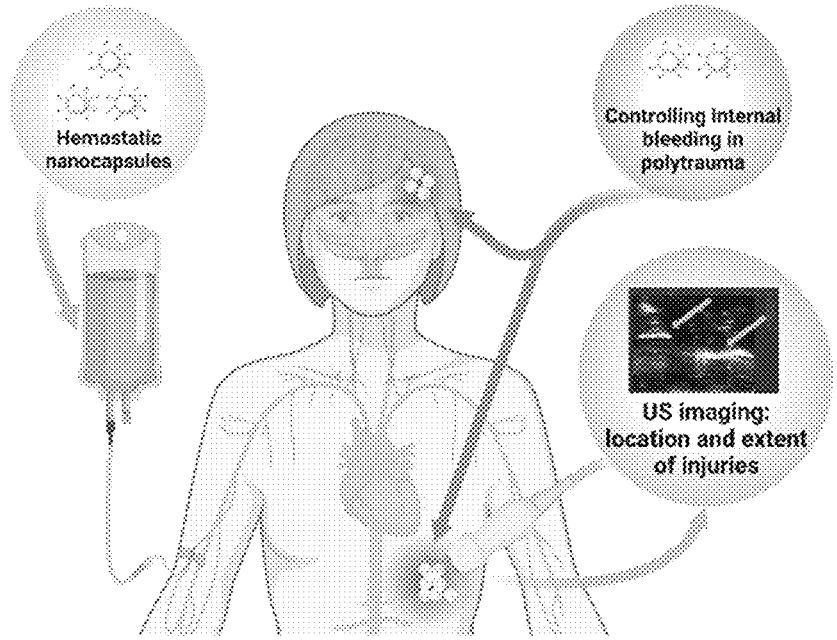
FIG. 6: Schematic of application of hemostatic nanocapsules and ultrasound in austere environments. The nanocapsules stop bleeding and become part of the clots. They are bright on ultrasound so we can see them, allowing greater resolution of the injuries. The nanocapsules are degradable and can be stored at room temperature.

Results a. Synthesis and Characterization of PEGylated Polyurethane Nanocapsules To develop hemostatic nanoparticles that do not lead to hypersensitivity reactions, PEGylated polyurethane nanocapsules were prepared through interfacial polymerization by modifying a previously published protocol [19, 23]. To achieve the hemostatic attribute, a NHS/EDC-based bioconjugation technique was utilized to conjugate the carboxyl end group of the exposed PEG on the nano surface with the primary amine group of the peptide motif GRGDS (FIGS. 1A-1B). The method of preparing these nanocapsules is a modified form of synthesizing the on-demand and long-term drug delivery nanocapsules [19]. This synthetic route allows the producer to control and vary the size, PEGylation, and peptide density of the nanocapsules.

The nanocapsules were characterized to determine the size and zeta-potential and to confirm the presence of PEG. The dynamic light scattering (DLS) data for the nanocapsules indicated that the nanocapsules were close to 150-250 nm in size and the zeta-potential changes based on the surface composition (FIG. 2 B). As previously observed [19], the nanocapsules in DLS show two peaks, with most nanocapsules in the size range mentioned. A very small population of the nanocapsules had a smaller size of less than 10 nm. As the nanocapsules are PEGylated, the zeta-potential increases from the highly negative zeta-potential of −47.3 mV observed in the non-PEGylated nanocapsules with increasing amount of PEG. Surprisingly, despite the high zeta potentials (in a range from −55 mV to −25 mV), the polyurethane-based nanocapsules do not show complement activation. The TEM of the nanocapsules was also consistent with the size of the particles observed in DLS (FIG. 2C). As the nanocapsules were modified by PEGylation, 1H-NMR was used to confirm the presence of the PEG and then quantify the amount present on the surface. To do that, the lyophilized nanocapsules were resuspended in deuterated water and the PEGylated and non-PEGylated samples were used to generate the peaks. The peak corresponding to PEG appears at 3.572 ppm, which remains absent in the NMR peak for non-PEGylated polyurethane nanocapsules (not shown herein). The moles of PEG in the sample are calculated compared to the IPDI moles in the sample based on the peak observed for its cyclohexyl ring at 1.41-1.42 ppm. Increasing the amount of PEG to the synthesis leads to an increase in the amount of the chain conjugated to the surface (FIG. 2B).

The peptide density on the nanocapsules studied here is approximately 35 µg per mg of nanocapsules.

b. Evaluating Changes in Complement Protein C5a In Vitro

To further confirm that the nanomaterials do not lead to hypersensitivity responses due to initial infusion reactions, how the complement proteins change in vitro was quantified. Complement-protected human serum with the PEGylated and non-PEGylated nanocapsules was incubated based on a previously established protocol [22]. The normalized change was determined compared to the C5a levels observed for complement-protected human serum incubated with PBS only. The change in complement protein remained least for the highly PEGylated polyurethane nanocapsules and the non-PEGylated nanocapsules (FIG. 3B). The highest change for zymosan, a known complement activator [24], and positive control in this study was observed (FIG. 3B). For highly PEGylated polyurethane nanocapsules with a dual brush length of 5000 Da PEG and 3400 Da PEG, with the former molecular weight present at a higher ratio, the complement protein C5a changes the least. While bare PLA nanocapsules can lead to as much activation as observed for the complement activator zymosan, polyurethane nanocapsules do not trigger any C5a increases even before modification, and PEGylation and conjugation of a RGD peptide (GRGDS) does not lead to C5a increases. With the polyurethane nanocapsules, changes observed for both the PEGylated and non-PEGylated counterparts remained lower than the PEG-PLA nanocapsules (FIG. 3C) and even close to the observed levels for the serum incubated with PBS only. Hence, it is hypothesized that the polyurethane nanocapsules, based on their in vitro findings, should lead to the least level of changes in complement proteins upon contact with blood and avoid complement-mediated infusion reactions in vivo.

c. Validating the Hemostatic Activity Through In Vitro Coagulation Assay

As hemostatic nanocapsules are administered intravenously, the nanoparticles would immediately encounter blood proteins. As a result, the PEGylated polyurethane nanocapsules seem like a feasible choice based on the low levels of complement proteins detected in vitro. The PEGylated nanocapsules were utilized for conjugating the peptide motif GRGDS. The hemostatic activity of these nanocapsules was then evaluated in vitro. The in vitro coagulation assay was carried out using the NATEM test of ROTEM for citrated blood collected from Sprague-Dawley rats through cardiac puncture. The clotting time (CT) and clot formation time (CFT) in total gives the time required to reach a 20 mm clot thickness, and that is used as a parameter of evaluation. The vehicle solution, the minimum essential medium supplemented with 1-glutamine only, was used as a control. The normalized change was determined compared to the vehicle control for the control nanocapsules without any peptide motif attached and the hemostatic nanocapsules (FIGS. 4A-4C). The change was significantly different and lower for the hemostatic nanocapsules at a 5 mg/ml concentration. At a lower concentration of 2.5 mg/ml, the hemostatic nanocapsules still result in a lower value for normalized CT+CFT; however, the change is not significantly different. Therefore, it is concluded that the polyurethane-based hemostatic nanocapsules are not only able to avoid complement-mediated infusion reactions but also able to display effective hemostatic activity.

d. Cytokine Response

The hemostatic polyurethane nanocapsules were investigated for cytokine activation using heparinized human whole blood and no signs of activation associated with infusion reactions was observed although activation was seen for polyester and control groups (data not shown).

Discussion

A nanoparticle upon intravenous infusion gets immediately engulfed in a protein corona, and the subsequent interaction can lead to complement-mediated hypersensitivity responses. This complement-mediated response, often termed an infusion reaction [25, 26], is of concern for nanoparticle systems broadly. The vast differences in materials and surface architecture indicate that materials properties impact this innate immune response [13, 27-30]. The hypersensitivity reaction is usually due to the first infusion, and as the system gets multiple exposures through subsequent bolus administrations, such reactions can be controlled [31]. However, for many nanoparticle infusions, the dosage must be high enough and delivered as a single bolus dose, where desensitization would not be possible. One such nanoparticle system is the hemostatic nanoparticles. The nanoparticles can reduce bleeding by almost 50% and significantly improve survival in major femoral artery injury models for rodents following intravenous administration [5]. Moreover, the hemostatic nanoparticles are designed such that they are safe and stable at room temperature [32]. Administering the hemostatic nanoparticles after traumatic injury due to blasts can mitigate internal bleeding and improve the pathologic outcomes [6]. However, the PLGA-based hemostatic nanoparticles may lead to hypersensitivity reactions, especially in large animal models [7]. Previous work with the hemostatic nanoparticles has shown that highly negative or highly positive nanoparticles cause complement activation leading to vasodilation [7]. Tuning the zeta-potential of the nanoparticles modulated the hypersensitivity responses; however, the effectiveness in avoiding the complement activation was only within a low particle dosage range [7]. Hence, there is a growing need for safer materials for nanomedicine that do not lead to initial infusion reactions, not only for the hemostatic nanoparticles but for nanomedicine in general that would be administered intravenously. To address that, a polyurethane-based hemostatic nanocapsule system has been designed and the impact of polyurethane nanocapsules on complement activation and coagulation activity in vitro evaluated.

Polyurethane nanocapsules were prepared by forming polyurethane linkages between aromatic isocyanate groups and aliphatic diols [19], and the materials based on the ratio of the hard and soft segments [33] present leads to soft rubbery elastomers. Polyurethane nanocapsules as drug delivery vehicles have gained popularity due to the scope of controlled release profile for therapeutics of interest utilizing stimuli. Based on the macromers selected to form the nanomaterial, there is scope to modulate the system to achieve biocompatibility [33]. In order to understand whether polyurethane nanomaterials developed with the goal of intravenous administration would lead to complement-mediated hypersensitivity response, the change in complement protein C5a in vitro was assessed. As the complement pathways are activated, C3 convertase is generated, which triggers the release of anaphylatoxins C3a and C5a [10]. The anaphylatoxins are pro-inflammatory and lead to degranulation of mast cells and production of histamines [9, 34], vasodilation, increased permeability of blood vessels [35] among some of many impacts of complement activation. The polyurethane-based systems were compared with and without PEGylation to poly(lactic acid)-based nanomaterials which are more prone to complement activation. Compared to highly reactive poly(lactic acid) cores, both PEGylated and non-PEGylated polyurethane lead to the least amount of complement protein C5a. The levels remained close to the observations in heparinized human whole blood incubated with PBS. Compared to previous studies involving PLGA-PLL-PEG hemostatic nanomaterials, where signs of complement activation were observed in vivo [7], the change in complement protein C5a was 3-4 folds higher in vitro [22] as well. As a result, the lesser complement activation in vitro indicates that the polyurethane nanoparticles could be expected to modulate the initial infusion reaction in vivo, making the system translatable and suitable for the hemostatic nano-systems.

The hemostatic activity of the nanocapsules was also evaluated through an in vitro coagulation assay using the NATEM test of ROTEM. The hemostatic nanocapsules have the peptide motif GRGDS conjugated to the PEG on the surface, which leads to the nanocapsules mimicking the role of fibrinogen, thereby attaching to activated platelets at the site of injury through the GPIIb/IIIa integrin. The citrated blood collected from Sprague Dawley rats was used to mimic those conditions, where the citration was reversed using the $CaCl_2$ reagent. The hemostatic nanocapsules at a concentration of 5 mg/mL could decrease the time required to form a 20 mm clot significantly compared to the control nanoparticles. This outcome highlights that a nanocapsule system can be developed that would potentially substantially or completely eliminate complement activation and at the same time impart hemostatic activity. There is further scope for tuning the peptide density and determining the optimum dosage required for the hemostatic nanocapsules. For example, it is known that peptide density [36] is crucial in determining the optimum dosage in vivo. Moreover, encapsulating anti-inflammatory molecules and triggering the release could be critical in controlling inflammation at the injury site.

Advantageously, the polyurethane-based hemostatic nanocapsules can be lyophilized and resuspended for use and are stable at room temperature, making it possible to transport them into the field. This is an important distinction that makes them well suited to austere conditions. The majority of contrast agents for ultrasound require refrigeration for storage.

Conclusion

One of the critical aspects of intravenously administered nanomaterials is that they encounter blood proteins immediately. This often causes initial infusion reactions as the body recognizes these as foreign materials. Hence understanding the properties of the material and how it interacts with the blood proteins can significantly impact the development and design of nanomaterials. A PEGylated polyurethane nanocapsule system was developed to identify the materials that would lead to the least amount of changes in the complement system. The initial assessment and comparison with conventional polyester-based nanomaterials indicate that the polyurethane nanocapsules lead to lower complement activation in vitro. Moreover, the peptide conjugated hemostatic nanocapsules lead to lower clot formation time in vitro, indicating that the system can form a stable clot plug faster to vehicle control and control nanoparticles. The polyurethane-based nanocapsule system described here opens the possibility for a safe and effective intravenous hemostatic treatment with clinical translation potential. The lack of complement activation coupled with the absence of pro-inflammatory cytokine responses (e.g., IL-1β, IL-6, IFN-γ, TNF-α, and IL-8) and hemostatic efficacy at low doses represents a significant advancement in the field. The nanocapsule system is not limited to hemostatic applications.

Example 2

Figure 7A:
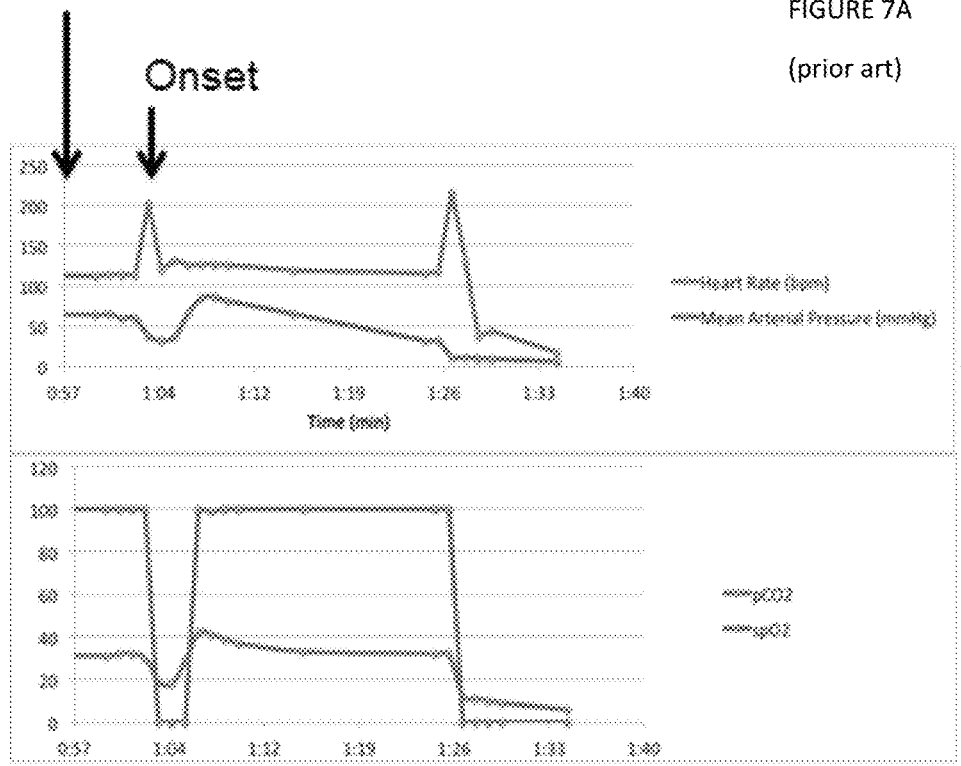
FIG. 7A: Physiological responses to intravenous administration of polyester nanoparticles that triggered complement-mediated infusion responses.
Figure 7B:
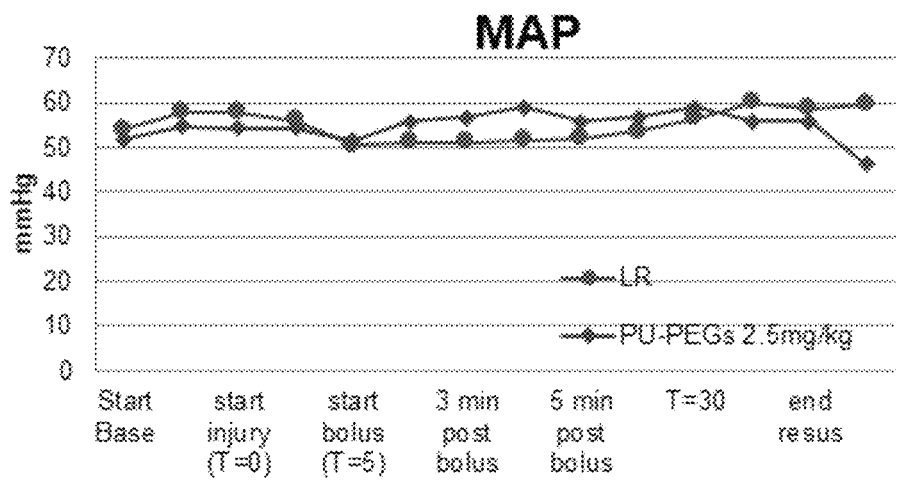
FIG. 7B: Administration of 2.5 mg/kg of the polyurethane-based nanocapsules as an intravenous bolus shows no significant changes in mean arterial pressure (MAP) following administration to the injured animal.
Figure 7C:
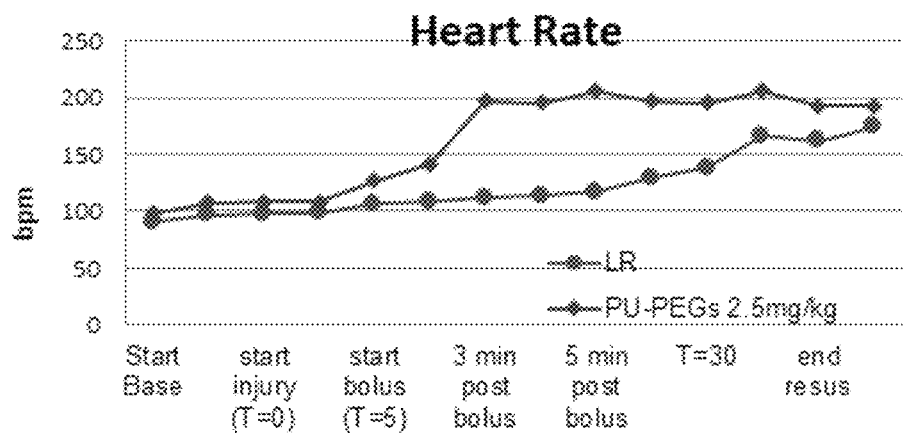
FIG. 7C: Administration of 2.5 mg/kg of the polyurethane-based nanocapsules as an intravenous bolus shows no significant changes in the heart rate following administration to the injured animal.
Figure 7D:
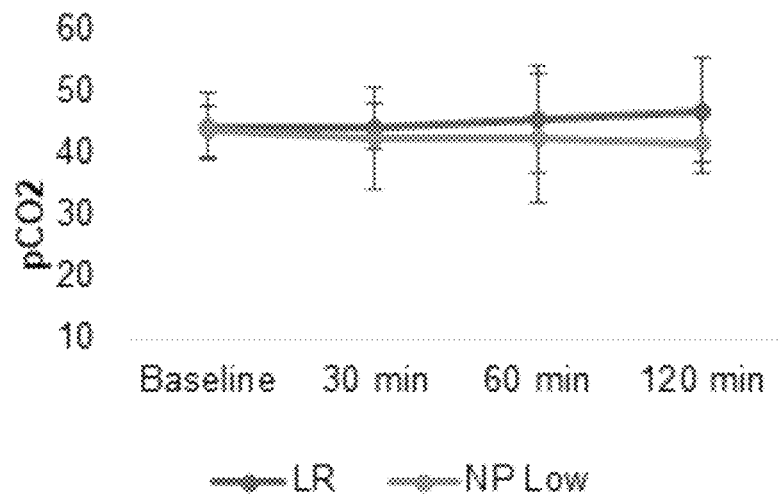
FIG. 7D: Administration of 2.5 mg/kg of the polyurethane-based nanocapsules as an intravenous bolus shows no significant changes in the $pCO_2$ blood gases following administration to the injured animal.
Figure 7E:
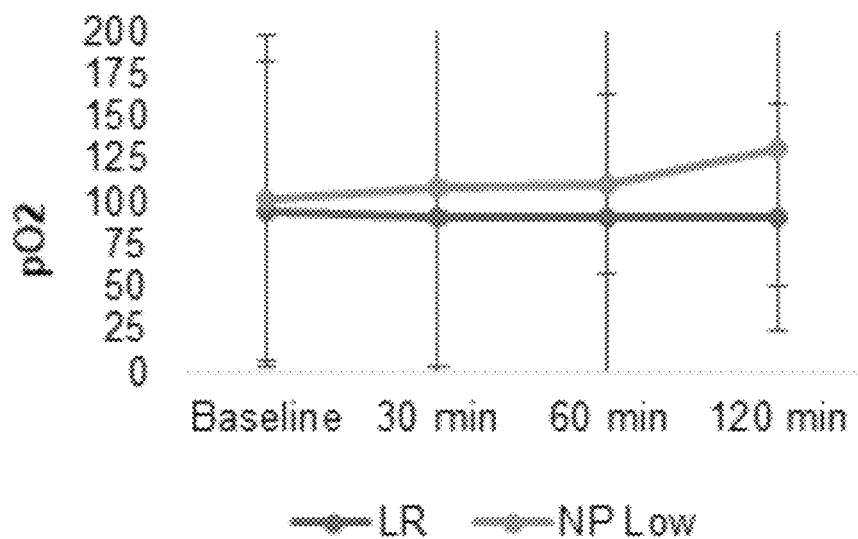
FIG. 7E: Administration of 2.5 mg/kg of the polyurethane-based nanocapsules as an intravenous bolus shows no significant changes in the $PO_2$ blood gases following administration to the injured animal.

The polyurethane nanocapsule-based hemostatic nanoparticle did not show complement activation in vitro, but the question remained how they would perform in a porcine trauma model. To test this, the polyurethane hemostatic nanocapsules were administered following a porcine polytrauma. With a polyester nanoparticle, an intravenous bolus of 2 mg/kg triggered significant physiological changes even in a naïve animal (FIG. 7A) and was lethal in a porcine liver trauma at doses above 4 mg/kg. In contrast, there are no signs of significant physiological changes at either the 2.5 mg/kg (FIG. 7B-E) or at 5 or 8 mg/kg dose of polyurethane nanoparticles (data not shown), and the animal survived to the end of the experiment without incident. Accordingly, initial testing suggests that the hemostatic nanocapsules described herein can be safely administered to large and small animals.

Example 3

Figure 9A:
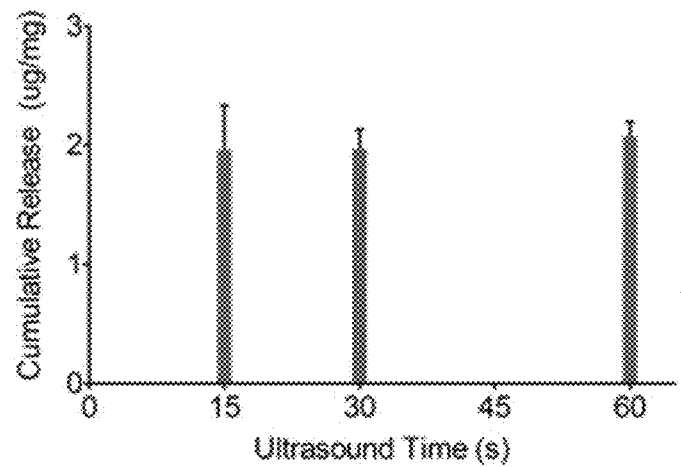
FIG. 9A: Release of a model drug (acriflavine) from polyurethane-based nanocapsules by ultrasound via a Ellex Eye Cubed system. Ultrasound triggers a substantial release (20× passive release) with 15 seconds of application at 90 dB and 10 MHz.
Figure 9B:
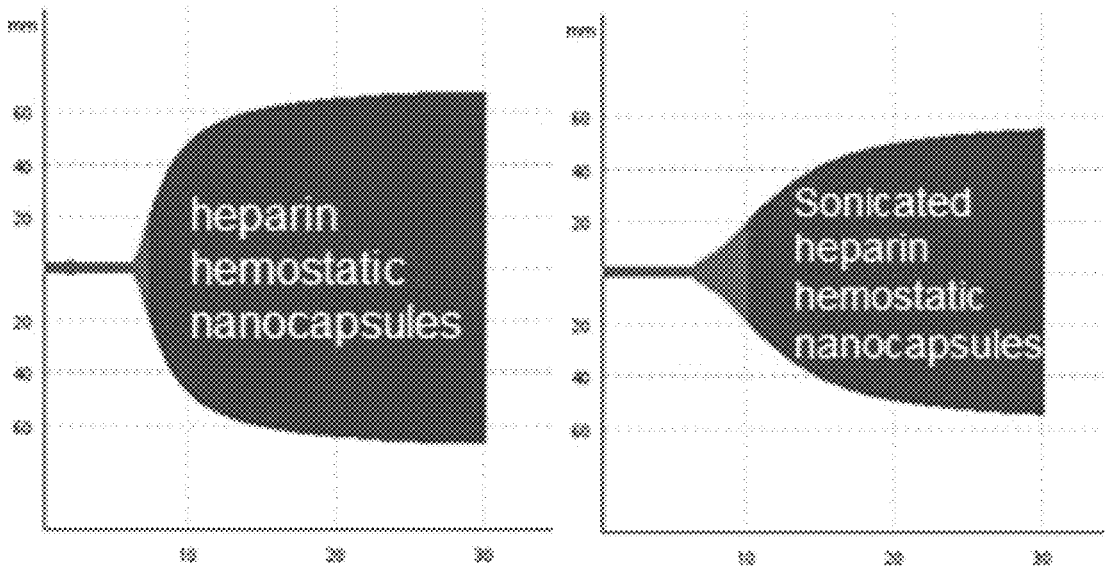
FIG. 9B: ROTEM curves for heparin-containing hemostatic nanocapsules and sonicated heparin-containing hemostatic nanocapsules. Heparin-containing nanocapsules are as procoagulatory as hemostatic nanocapsules without heparin. Sonication (60s) releases 0.6 mg of heparin per mg of nanocapsules, extending the clotting time as expected.
Figure 9C:
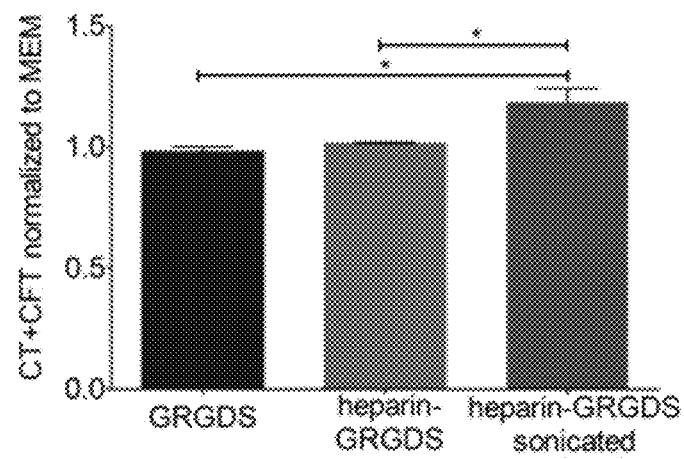
FIG. 9C: Clotting time (n=3). Heparin can be encapsulated in the hemostatic nanocapsules. When encapsulated, the hemostatic nanocapsules retain their hemostatic behavior (see, e.g., GRGDS vs. heparin-GRGDS). However, upon application of ultrasound, the heparin is released making the system an anticoagulant system (see, e.g., heparin-GRGDS sonicated vs. heparin-GRGDS). Thus, the system can switch from a procoagulant to an anticoagulant state with the application of ultrasound.

The hemostatic efficacy of the PEGylated polyurethane nanocapsules coupled with their ability to be visualized via ultrasound provides the foundation for their use in hemostatic applications. Their ability to be loaded with heparin and triggered via ultrasound to release the drug to impact clotting makes them suitable for a switchable pro/anticoagulant system (see, FIGS. 9B and 9C). In FIG. 9B, ROTEM curves show that heparin-containing nanocapsules are as procoagulatory as hemostatic nanocapsules without heparin. Sonication (60s) releases 0.6 mg of heparin per mg of nanocapsules, extending the clotting time as expected. FIG. 9C shows that when encapsulated, the hemostatic nanocapsules retain their hemostatic behavior (see, e.g., GRGDS vs. heparin-GRGDS). However, upon application of ultrasound, the heparin is released making the system an anticoagulant system (see, e.g., heparin-GRGDS sonicated vs. heparin-GRGDS). Thus, the system can switch from a procoagulant to an anticoagulant state with the application of ultrasound.

Example 4

While dexamethasone is potent and easily delivered, it has such a challenging track record with side effects from systemic delivery that there is limited enthusiasm even for local delivery of this steroid. As an alternative, the nanocapsules described herein can be used to deliver TEMPOL (also known as 4-hydroxy-TEMPO or 4-hydroxy-2,2,6,6-tetramethylpiperidin-1-yl)oxyl, a free radical scavenger, that has been shown to be neuroprotective after acute central nervous system disease and traumatic injury. It is chemically similar to dexamethasone, so formulations are analogous, but it is more specific for the damage associated with TBI and is potentially safer. Its' antioxidant function has led to microvascular and axonal protection following single and repeated brain injury.

Previously, TEMPOL has been delivered from a range of polymers including PLGA nanoparticle. It is extremely robust and chemically stable which makes it a particularly attractive molecule for encapsulation in hemostatic PEGylated polyurethane nanocapsules.

Figure 10:
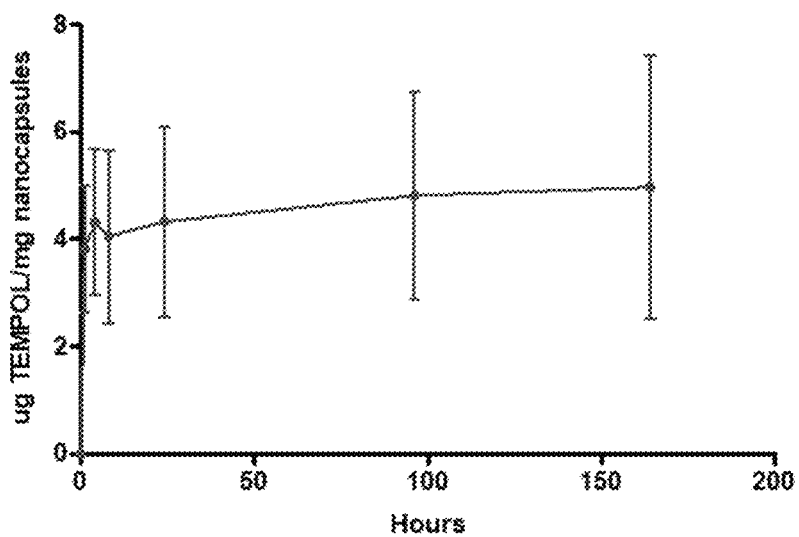
FIG. 10: A release curve for hemostatic PEGylated polyurethane nanocapsules loaded with 4 g/mg TEMPOL.

TEMPOL was encapsulated at a concentration of (4 µg/mg) in the hemostatic PEGylated polyurethane nanocapsules described herein, and the release of the TEMPOL was monitored over time. As seen in FIG. 10, all of the drug was released within the first hour. Advantageously, the application of ultrasound can be used to trigger on demand release of the TEMPOL at the site of the bleeding. It was further determined that upwards of 100 µg/mg could be loaded in the hemostatic PEGylated polyurethane nanocapsules described herein.

Example 5

Figure 11:
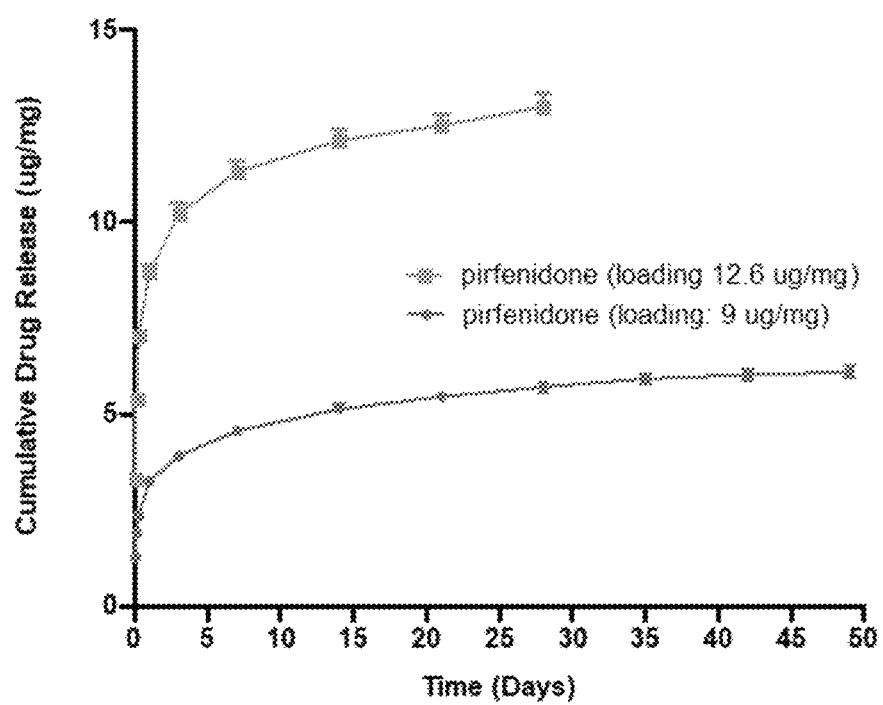
FIG. 11: Release curves for hemostatic PEGylated polyurethane nanocapsules loaded with 12.6 g/mg and 9 μg/mg pirfenidone.

Pirfenidone, which has potential for wound healing, was encapsulated in the hemostatic PEGylated polyurethane nanocapsules described herein, and the cumulative release of the pirfenidone was monitored over time. As seen in FIG. 11, a formulation comprising 12.6 µg pirfenidone per mg of hemostatic PEGylated polyurethane nanocapsules released the drug over 30 days. A formulation comprising 9 µg of pirfenidone per mg of hemostatic PEGylated polyurethane nanocapsules released the drug for over 50 days. Advantageously, the application of ultrasound can be used to trigger on demand release of the pirfenidone.

Although the invention has been variously disclosed herein with reference to illustrative embodiments and features, it will be appreciated that the embodiments and features described hereinabove are not intended to limit the invention, and that other variations, modifications and other embodiments will suggest themselves to those of ordinary skill in the art, based on the disclosure herein. The invention therefore is to be broadly construed, as encompassing all such variations, modifications and alternative embodiments within the spirit and scope of the claims hereafter set forth.

REFERENCES

1. Kauvar, D. S.; Lefering, R.; Wade, C. E., Impact of hemorrhage on trauma outcome: an overview of epidemiology, clinical presentations, and therapeutic considerations. *Journal of Trauma and Acute Care Surgery* 2006, 60 (6), S3-S11.
2. Cloonan, C. C., Treating traumatic bleeding in a combat setting. *Mil Med* 2004, 169 (12 Suppl), s8-s10.
3. Okada, K.; Matsumoto, H.; Saito, N.; Yagi, T.; Lee, M., Revision of 'golden hour' for hemodynamically unstable trauma patients: an analysis of nationwide hospital-based registry in Japan. *Trauma Surg Acute Care Open* 2020, 5 (1), e000405 DOI: 10.1136/tsaco-2019-000405.
4. Bertram, J. P.; Williams, C. A.; Robinson, R.; Segal, S. S.; Flynn, N. T.; Lavik, E. B., Intravenous hemostat: nanotechnology to halt bleeding. *Sci Transl Med* 2009, 1 (11), 11ra22 DOI: 10.1 126/scitranslmed.3000397.
5. Shoffstall, A. J.; Atkins, K. T.; Groynom, R. E.; Varley, M. E.; Everhart, L. M.; Lashof-Sullivan, M. M.; Martyn-Dow, B.; Butler, R. S.; Ustin, J. S.; Lavik, E. B., Intravenous Hemostatic Nanoparticles Increase Survival Following Blunt Trauma Injury. *Biomacromolecules* 2012, 13 (11), 3850-3857 DOI: 10.1021/bm3013023.
6. Hubbard, W. B.; Lashof-Sullivan, M. M.; Lavik, E. B.; VandeVord, P. J., Steroid-Loaded Hemostatic Nanoparticles Combat Lung Injury after Blast Trauma. *ACS Macro Letters* 2015, 4 (4), 387-391 DOI: 10.1021/acsmacrolett.5b00061.
7. Onwukwe, C.; Maisha, N.; Holland, M.; Varley, M.; Groynom, R.; Hickman, D.; Uppal, N.; Shoffstall, A.; Ustin, J.; Lavik, E., Engineering Intravenously Administered Nanoparticles to Reduce Infusion Reaction and Stop Bleeding in a Large Animal Model of Trauma. *Bioconjugate chemistry* 2018, 29 (7), 2436-2447 DOI: 10.1021/acs.bioconjchem.8b00335.
8. Ricklin, D.; Lambris, J. D., Complement in immune and inflammatory disorders: pathophysiological mechanisms. *J Immunol* 2013, 190 (8), 3831-8 DOI: 10.4049/jimmunol.1203487.
9. Benjamini, E., *Immunology: a short course. Vol.* 77.
10. Moghimi, S. M.; Simberg, D., Complement activation turnover on surfaces of nanoparticles. *Nano Today* 2017, 15, 8-10 DOI: 10.1016/j.nantod.2017.03.001.
11. Szebeni, J., Hemocompatibility testing for nanomedicines and biologicals: predictive assays for complement mediated infusion reactions. *European Journal of Nanomedicine* 2012, 4 (1), DOI: 10.1515/ejnm-2012-0002.
12. Chanan-Khan, A.; Szebeni, J.; Savay, S.; Liebes, L.; Rafique, N. M.; Alving, C. R.; Muggia, F. M., Complement activation following first exposure to pegylated liposomal doxorubicin (Doxil): possible role in hypersensitivity reactions. *Ann Oncol* 2003, 14 (9), 1430-7 DOI: 10.1093/annonc/mdg374.
13. Cullion, K.; Rwei, A. Y.; Kohane, D. S., Ultrasound-triggered liposomes for on-demand local anesthesia. *Ther Deliv* 2018, 9 (1), 5-8.
14. Xu, J.; Tu, H.; Ao, Z.; Chen, Y.; Danehy, R.; Guo, F., Acoustic disruption of tumor endothelium and on-demand drug delivery for cancer chemotherapy. *Nanotechnology* 2019, 30 (15), 154001.
15. Ouyang, X.; Huang, X.; Pan, Q.; Zuo, C.; Huang, C.; Yang, X.; Zhao, Y., Synthesis and characterization of triethylene glycol dimethacrylate nanocapsules used in a self-healing bonding resin. *J Dent* 2011, 39 (12), 825-33 DOI: 10.1016/j.jdent.2011.09.001.
16. Pramanik, S. K.; Sreedharan, S.; Singh, H.; Khan, M.; Tiwari, K.; Shiras, A.; Smythe, C.; Thomas, J. A.; Das, A., Mitochondria Targeting Non-Isocyanate-Based Polyurethane Nanocapsules for Enzyme-Triggered Drug Release. *Bioconjug Chem* 2018, 29 (11), 3532-3543 DOI: 10.1021/acs.bioconjchem.8b00460.
17. Boffito, M.; Torchio, A.; Tonda-Turo, C.; Laurano, R.; Gisbert-Garzaran, M.; Berkmann, J. C.; Cassino, C.; Manzano, M.; Duda, G. N.; Vallet-Regi, M.; Schmidt-Bleek, K.; Ciardelli, G., Hybrid Injectable Sol-Gel Systems Based on Thermo-Sensitive Polyurethane Hydrogels Carrying pH-Sensitive Mesoporous Silica Nanoparticles for the Controlled and Triggered Release of Therapeutic Agents. *Front Bioeng Biotechnol* 2020, 8, 384 DOI: 10.3389/fbioe.2020.00384.
18. Niu, Y.; Stadler, F. J.; Song, J.; Chen, S.; Chen, S., Facile fabrication of polyurethane microcapsules carriers for tracing cellular internalization and intracellular pH-triggered drug release. *Colloids Surf B Biointerfaces* 2017, 153, 160-167 DOI: 10.1016/j.colsurfb.2017.02.018.
19. Menikheim, S.; Leckron, J.; Bernstein, S.; Lavik, E. B., On-Demand and Long-Term Drug Delivery from Degradable Nanocapsules. *ACS Applied Bio Materials* 2020, 3 (11), 7369-7375 DOI: 10.1021/acsabm.0c01130.
20. Zhou, L.; Liang, D.; He, X.; Li, J.; Tan, H.; Li, J.; Fu, Q.; Gu, Q., The degradation and biocompatibility of pH-sensitive biodegradable polyurethanes for intracellular multifunctional antitumor drug delivery. *Biomaterials* 2012, 33 (9), 2734-45 DOI: 10.1016/j.biomaterials.2011.11.009.
21. Bernacca, G.; Gulbransen, M.; Wilkinson, R.; Wheatley, D., In vitro blood compatibility of surface-modified polyurethanes. *Biomaterials* 1998, 19 (13), 1151-1165.

22. Maisha, N.; Coombs, T.; Lavik, E., Development of a Sensitive Assay to Screen Nanoparticles in Vitro for Complement Activation. *ACS Biomaterials Science & Engineering* 2020, 6 (9), 4903-4915 DOI: 10.1021/acsbiomaterials.0c00722.
23. Guo, J.; Pan, Q.; Huang, C.; Zhao, Y.; Ouyang, X.; Huo, Y.; Duan, S., The role of surfactant and costabilizer in controlling size of nanocapsules containing TEGDMA in miniemulsion. *Journal of Wuhan University of Technology-Mater. Sci. Ed.* 2009, 24 (6), 1004-1006 DOI: 10.1007/s11595-009-7004-2.
24. Fearon, D. T.; Austen, K. F., Activation of the alternative complement pathway due to resistance of zymosan-bound. *Proceedings of the National Academy of Sciences* 1977, 74 (4), 1683-1687.
25. Wibroe, P. P.; Anselmo, A. C.; Nilsson, P. H.; Sarode, A.; Gupta, V.; Urbanics, R.; Szebeni, J.; Hunter, A. C.; Mitragotri, S.; Mollnes, T. E.; Moghimi, S. M., Bypassing adverse injection reactions to nanoparticles through shape modification and attachment to erythrocytes. *Nat Nanotechnol* 2017, 12 (6), 589-594 DOI: 10.1038/nnano.2017.47.
26. Szebeni, J.; Bed6cs, P.; Csukis, D.; Rosivall, L.; Bünger, R.; Urbanics, R., A porcine model of complement-mediated infusion reactions to drug carrier nanosystems and other medicines. *Advanced Drug Delivery Reviews* 2012, 64 (15), 1706-1716 DOI: 10.1016/j.addr.2012.07.005.
27. Wang, G.; Chen, F.; Banda, N. K.; Holers, V. M.; Wu, L.; Moghimi, S. M.; Simberg, D., Activation of Human Complement System by Dextran-Coated Iron Oxide Nanoparticles Is Not Affected by Dextran/Fe Ratio, Hydroxyl Modifications, and Crosslinking. *Front Immunol* 2016, 7, 418 DOI: 10.3389/fimmu.2016.00418.
28. Ruiz, A.; Alpizar, A.; Beola, L.; Rubio, C.; Gavilin, H.; Marciello, M.; Rodriguez-Ramiro, I.; Ciordia, S.; Morris, C. J.; Morales, M. d. P., Understanding the Influence of a Bifunctional Polyethylene Glycol Derivative in Protein Corona Formation around Iron Oxide Nanoparticles. *Materials* 2019, 12 (14), 2218.
29. Hamad, I.; Christy Hunter, A.; Rutt, K. J.; Liu, Z.; Dai, H.; Moein Moghimi, S., Complement activation by PEGylated single-walled carbon nanotubes is independent of C1q and alternative pathway turnover. *Mol Immunol* 2008, 45 (14), 3797-803 DOI: 10.1016/j.molimm.2008.05.020.
30. Hamad, I.; Al-Hanbali, O.; Hunter, A. C.; Rutt, K. J.; Andresen, T. L.; Moghimi, S. M., Distinct polymer architecture mediates switching of complement activation pathways at the nanosphere-serum interface: implications for stealth nanoparticle engineering. *ACS nano* 2010, 4 (11), 6629-6638.
31. Szebeni, J.; Bedocs, P.; Urbanics, R.; Bunger, R.; Rosivall, L.; Toth, M.; Barenholz, Y., Prevention of infusion reactions to PEGylated liposomal doxorubicin via tachyphylaxis induction by placebo vesicles: a porcine model. *J Control Release* 2012,160 (2), 382-7 DOI: 10.1016/j.jconrel.2012.02.029.
32. Lashof-Sullivan, M.; Holland, M.; Groynom, R.; Campbell, D.; Shoffstall, A.; Lavik, E., Hemostatic Nanoparticles Improve Survival Following Blunt Trauma Even after 1 Week Incubation at 50 (°)C. *ACS biomaterials science & engineering* 2016, 2 (3), 385-392 DOI: 10.1021/acsbiomaterials.5b00493.
33. Cherng, J. Y.; Hou, T. Y.; Shih, M. F.; Talsma, H.; Hennink, W. E., Polyurethane-based drug delivery systems. *Int J Pharm* 2013, 450 (1-2), 145-62 DOI: 10.1016/j.ijpharm.2013.04.063.
34. Peng, Q.; Li, K.; Sacks, S. H.; Zhou, W., The role of anaphylatoxins C3a and C5a in regulating innate and adaptive immune responses. *Inflammation & Allergy-Drug Targets (Formerly Current Drug Targets-Inflammation & Allergy)* 2009, 8 (3), 236-246 DOI: 10.2174/187152809788681038.
35. Ember, J.; Jagels, M.; Hugh, T.; Volanakis, J.; Frank, M., The human complement system in health and disease. *Marcel Dekker* 1998, 241-84.
36. Shoffstall, A. J.; Everhart, L. M.; Varley, M. E.; Soehnlen, E. S.; Shick, A. M.; Ustin, J. S.; Lavik, E. B., Tuning Ligand Density on Intravenous Hemostatic Nanoparticles Dramatically Increases Survival Following Blunt Trauma. *Biomacromolecules* 2013, 14 (8), 2790-2797 DOI: 10.1021/bm400619v.
37. Hubbard, W. B., M. Lashof-Sullivan, S. Greenberg, C. Norris, J. Eck, E. Lavik, and P. VandeVord, *Hemostatic nanoparticles increase survival, mitigate neuropathology and alleviate anxiety in a rodent blast trauma model.* Sci Rep, 2018. 8(1): p. 10622. PMID: 30006635. pmcid: PMC6045585.
38. Gando, S., M. Levi, and C. H. Toh, *Disseminated intravascular coagulation.* Nat Rev Dis Primers, 2016. 2: p. 16037. PMID: 27250996.
39. Cardenas, J. C., C. E. Wade, and J. B. Holcomb, *Mechanisms of trauma-induced coagulopathy.* Curr Opin Hematol, 2014. 21(5): p. 404-9. PMID: 25010798.
40. Innerhofer, P., D. Fries, M. Mittermayr, N. Innerhofer, D. von Langen, T. Hell, G. Gruber, S. Schmid, B. Friesenecker, I. H. Lorenz, M. Strohle, V. Rastner, S. Trubsbach, H. Raab, B. Treml, D. Wally, B. Treichl, A. Mayr, C. Kranewitter, and E. Oswald, *Reversal of trauma-induced coagulopathy using first-line coagulation factor concentrates or fresh frozen plasma (RETIC): a single-centre, parallel-group, open-label, randomised trial.* Lancet Haematol, 2017. 4(6): p. e258-e271. PMID: 28457980.
41. Samuels, J. M., E. E. Moore, C. C. Silliman, A. Banerjee, M. J. Cohen, A. Ghasabyan, J. Chandler, J. R. Coleman, and A. Sauaia, *Severe traumatic brain injury is associated with a unique coagulopathy phenotype.* J Trauma Acute Care Surg, 2019. 86(4): p. 686-693. PMID: 30601456. pmcid: PMC6682404.
42. King, D. R., S. M. Cohn, and K. G. Proctor, *Changes in intracranialpressure, coagulation, and neurologic outcome after resuscitation from experimental traumatic brain injury with hetastarch.* Surgery, 2004. 136(2): p. 355-63. PMID: 15300202.
43. Kumar, M. A., *Coagulopathy associated with traumatic brain injury.* Curr Neurol Neurosci Rep, 2013. 13(11): p. 391. PMID: 24046182.
44. Yang, Q., C. Zhou, Q. Zhao, Z. Chu, D. P. Yang, and N. Jia, *Sonochemical assisted synthesis of dual functional BSA nanoparticle for the removal of excessive bilirubin and strong anti-tumor effects.* Mater Sci Eng C Mater Biol Appl, 2019. 100: p. 688-696. PMID: 30948105.
45. Sodipo, B. K. and A. A. Aziz, *One minute synthesis of amino-silanefunctionalized superparamagnetic iron oxide nanoparticles by sonochemical method.* Ultrason Sonochem, 2018. 40(Pt A): p. 837-840. PMID: 28946493.
46. Sanchez Ramirez, D. O., A. Varesano, R. A. Carletto, C. Vineis, I. Perelshtein, M. Natan, N. Perkas, E. Banin, and A. Gedanken, *Antibacterial properties of polypyrrole-treated fabrics by ultrasound deposition.* Mater Sci Eng C Mater Biol Appl, 2019. 102: p. 164-170. PMID: 31146987.
47. Abdel-Rahman, L. H., A. M. Abu-Dief, R. M. El-Khatib, and S. M. Abdel-Fatah, *Sonochemical synthesis, DNA* binding, antimicrobial evaluation and in vitro anticancer activity of three new nano-sized Cu(II), Co(II) and Ni(II) chelates based on tri-dentate NOO imine ligands as precursors for metal oxides. J Photochem Photobiol B, 2016. 162: p. 298-308. PMID: 27395793.
48. Jeremias Junior, S. L., G. L. Camanho, A. C. Bassit, A. Forgas, S. J. Ingham, and R. J. Abdalla, *Low-intensity pulsed ultrasound accelerates healing in rat calcaneus tendon injuries*. J Orthop Sports Phys Ther, 2011. 41(7): p. 526-31. PMID: 21335926.
49. Kamimura, H. A., S. Wang, H. Chen, Q. Wang, C. Aurup, C. Acosta, A. A. Carneiro, and E. E. Konofagou, *Focused ultrasound neuromodulation of cortical and subcortical brain structures using 1.9 MHz*. Med Phys, 2016. 43(10): p. 5730. PMID: 27782686. pmcid: PMC5045443.
50. Legon, W., L. Ai, P. Bansal, and J. K. Mueller, *Neuromodulation with single-element transcranial focused ultrasound in human thalamus*. Hum Brain Mapp, 2018. 39(5): p. 1995-2006. PMID: 29380485.
51. Yeung, C. K., X. Guo, and Y. F. Ng, *Pulsed ultrasound treatment accelerates the repair of Achilles tendon rupture in rats*. J Orthop Res, 2006. 24(2): p. 193-201. PMID: 16435348.
52. Ruhnke, H., T. Eckey, M. K. Bohlmann, M. P. Beldoch, A. Neumann, A. Agic, J. Hagele, K. Diedrich, J. Barkhausen, and P. Hunold, *MR-guided HIFU treatment of symptomatic uterine fibroids using novel feedback-regulated volumetric ablation: effectiveness and clinical practice*. Rofo, 2013. 185(10): p. 983-91. PMID: 24490234.
53. Stewart, E. A., J. Rabinovici, C. M. Tempany, Y. Inbar, L. Regan, B. Gostout, G. Hesley, H. S. Kim, S. Hengst, and W. M. Gedroyc, *Clinical outcomes of focused ultrasound surgery for the treatment of uterine fibroids*. Fertil Steril, 2006. 85(1): p. 22-9. PMID: 16412721.
54. Vlaisavljevich, E., Y. Kim, S. Allen, G. Owens, S. Pelletier, C. Cain, K. Ives, and Z. Xu, *Image-Guided Non-invasive Ultrasound Liver Ablation Using Histotripsy: Feasibility Study in an In Vivo Porcine Model*. Ultrasound in Medicine & Biology, 2013. PMID: 23683406.
55. Vlaisavljevich, E., O. Aydin, Y. Y. Durmaz, K. W. Lin, B. Fowlkes, Z. Xu, and M. E. ElSayed, *Effects of Droplet Composition on Nanodroplet-Mediated Histotripsy*. Ultrasound Med Biol, 2016. 42(4): p. 931-46. PMID: 26774470.
56. Vlaisavljevich, E., O. Aydin, Y. Yuksel Durmaz, K. W. Lin, B. Fowlkes, M. ElSayed, and Z. Xu, *Effects of Ultrasound Frequency on Nanodroplet-Mediated Histotripsy*. Ultrasound Med Biol, 2015. 41(8): p. 2135-47. PMID: 25959056.
57. Xiang, Z., Y. Wang, Z. Ma, Z. Xin, R. Chen, Q. Shi, S. C. Wong, and J. Yin, *Inhibition of Inflammation-Associated Thrombosis with ROS-Responsive Heparin-DOCA/PVAX Nanoparticles*. Macromol Biosci, 2019. 19(8): p. e1900112. PMID: 31222912.
58. Fernandez-Moure, J., N. Maisha, E. B. Lavik, and J. Cannon, *The chemistry of lyophilized blood products*. Bioconjug Chem, 2018. 29(7): p. 2150-2160. PMID: 29791137.
59. Rocas, P.; Fernindez, Y.; Garcia-Aranda, N.; Foradada, L.; Calvo, P.; Avilés, P.; Guillón, M. J.; Schwartz, S., Jr.; Rocas, J.; Albericio, F.; Abasolo, I., Improved pharmacokinetic profile of lipophilic anti-cancer drugs using $\alpha v \beta 3$-targeted polyurethane-polyurea nanoparticles. *Nanomedicine* 2018, 14 (2), 257-267.

What is claimed is:
1. A method of identifying sites of traumatic bleeding and promoting clotting in a patient that may have experienced trauma, said method comprising:
administering a bolus of PEGylated polyurethane nanocapsules to the patient, wherein the PEGylated polyurethane nanocapsules comprise a substantially spherical shell of polyurethane surrounding a core, wherein a surface of the shell of polyurethane is substantially PEGylated, wherein the core comprises air, and wherein the PEGylated polyurethane nanocapsules participate in clot formation thus accumulating in sites of bleeding; and
scanning the patient using ultrasound to visualize the accumulated PEGylated polyurethane nanocapsules in vivo, to identify the sites of traumatic bleeding.
2. The method of claim 1, wherein the core further comprises at least one of air, a solution comprising at least one drug, a solution comprising at least one contrast agent, or a solution comprising at least one fluorinated compound that makes the system more ultrasound responsive.
3. The method of claim 1, wherein the nanocapsules comprise poly(ethylene glycol) (PEG) groups selected from carboxyl-PEG, methoxy-PEG, or a mixture of both.
4. The method of claim 1, wherein the shell comprising the polyurethane further comprises at least one encapsulated molecule.
5. The method of claim 4, wherein the at least one encapsulated molecule comprises at least one of TEMPOL, pirfenidone, an anticoagulant, an anti-inflammatory drug, an antibiotic, an antioxidant, or any combination thereof.
6. The method of claim 4, wherein the at least one encapsulated molecule comprises an anticoagulant selected from heparin, tissue type Plasminogen Activator (tPA), and argatroban.
7. The method of claim 1, wherein the PEGylated polyurethane nanocapsules further comprise peptide motifs conjugated to a carboxyl end group of a PEG group.
8. The method of claim 7, wherein the peptide motifs comprise a targeting peptide comprising an amine.
9. The method of claim 7, wherein the peptide motifs comprise an RGD peptide.
10. The method of claim 1, wherein the PEGylated polyurethane nanocapsules are hemostatic.
11. The method of claim 1, wherein the PEGylated polyurethane nanocapsules are administered intravenously, intraarterially, intrathecally, intradermally, intracavitarily, orally, rectally, intramuscularly, subcutaneously, intracisternally, intravaginally, intraperitonially, intravitreally, suprachoroidally, subconjunctivally, topically, buccally, and/or nasally.
12. The method of claim 1, wherein the bolus of PEGylated polyurethane nanocapsules administered is in a range from about 1 mg/kg to about 10 mg/kg.
13. A method of identifying sites of traumatic bleeding in a patient that may have experienced trauma and releasing an anticoagulant to the sites of traumatic bleeding, said method comprising:
administering a bolus of PEGylated polyurethane nanocapsules to a patient, wherein the PEGylated polyurethane nanocapsules comprise a substantially spherical shell of polyurethane surrounding a core, wherein a surface of the shell of polyurethane is substantially PEGylated, wherein the shell comprising the polyurethane further comprises encapsulated anticoagulant, wherein the core comprises air, and wherein the PEGylated polyurethane nanocapsules participate in clot formation thus accumulating in sites of bleeding;

scanning the patient using ultrasound to visualize the accumulated PEGylated polyurethane nanocapsules in vivo to identify the sites of traumatic bleeding; and applying ultrasound energy in proximity of the sites of traumatic bleeding to release an amount of anticoagulant from the PEGylated polyurethane nanocapsules to the sites of traumatic bleeding.

14. The method of claim 13, wherein the application of ultrasound energy is noninvasive.

15. The method of claim 13, wherein the application of ultrasound energy switches the anticoagulant from being a procoagulant to an anticoagulant.

16. The method of claim 13, wherein the anticoagulant is selected from heparin, tissue type Plasminogen Activator (tPA), and argatroban.

* * * * *